(12) United States Patent
Daniel et al.

(10) Patent No.: US 7,736,848 B2
(45) Date of Patent: Jun. 15, 2010

(54) CELLULAR TARGETS FOR TREATMENT OF RETROVIRAL INFECTION

(75) Inventors: Rene Daniel, Ambler, PA (US); Anna Marie Skalka, Princeton, NJ (US); Gary D. Kao, Wynnewood, PA (US); Giuseppe Nunnari, Cantania (IT); Roger J. Pomerantz, Chalfont, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 445 days.

(21) Appl. No.: 11/093,692

(22) Filed: Mar. 30, 2005

(65) Prior Publication Data

US 2006/0024694 A1    Feb. 2, 2006

Related U.S. Application Data

(63) Continuation-in-part of application No. PCT/US03/31164, filed on Sep. 30, 2003.

(60) Provisional application No. 60/414,791, filed on Sep. 30, 2002.

(51) Int. Cl.
 C12N 1/21    (2006.01)
 C12Q 1/701    (2006.01)
(52) U.S. Cl. .................... 435/5; 424/1.61; 435/339
(58) Field of Classification Search .................. None
 See application file for complete search history.

(56) References Cited

U.S. PATENT DOCUMENTS 6,033,902 A    3/2000    Haseltine et al. ......... 435/320.1
6,420,338 B1    7/2002    Schneider et al. ............. 514/12

FOREIGN PATENT DOCUMENTS

GB    2 362 952 A    12/2001
WO    WO 00/17386 A1    3/2000
WO    WO 01/92562 A2 *    12/2001

OTHER PUBLICATIONS

Shiloh, Feb. 2001,Current Opinion in Genetics and Development, vol. 11, p. 71-77.*
Asaad, N.A., et al., "Homologous recombination as a potential target for caffeine radiosensitization in mammalian cells: reduced caffeine radiosensitization in XRCC2 and XRCC3 mutants," *Oncogene*, 2000, 19, 5788-5800.
Blasina, A., et al., "Caffeine inhibits the checkpoint kinase ATM," *Curr. Biol.*, 1999, 9, 1135-1138.
Bohm, L., et al., "Inhibition of DNA repair by pentoxifylline and related methylxanthine derivatives," *Toxicology*, 2003, 193(1-2), 153-160 (abstract 1 page).
Boyd, K.E., et al., "Coexamination of site-specific transcription factor binding and promoter activity in living cells," *Mol. & Cell. Biol.*, 1999, 19(12), 8393-8399.

Brin, E., et al., "Modeling the late steps in HIV-1 retroviral integrase-catalyzed DNA integration," *J. of Biol. Chem.*, 2000, 275(50), 39287-39295.
Cliby, W.A., et al., "Overexpresion of a kinase-inactive ATR protein causes sensitivity to DNA-damaging agents and defects in cell cycle checkpoints," *EMBO J.*, 1998, 17(1), 159-169.
Cliby, W.A., et al., "S phase and $G_2$ arrests induced by topoisomerase I poisons are dependent on ATR kinase function," *J. Biol. Chem.*, 2002, 277(2), 1599-1606.
Coffin, J.M., et al., *Retroviruses*, Cold Spring Harbor Laboratory, 1997, Abstract 3 pages.
Cortez, D., et al., "Requirement of ATM-dependent phosphorylation of Brca 1 in the DNA damage response to double-strand breaks," *Science*, 1999, 286, 1162-1166.
Cortez, D., et al., "ATR and ATRIP: partners in checkpoint signaling," *Science*, 2001, 294, 1713-1716.
Daniel, R., et al., "A role for DNA-PK in retroviral DNA integration," *Science*, 1999, 284, 644-647.
Daniel, R., et al., "Wortmannin potentiates integrase-mediated killing of lymphocytes and reduces the efficiency of stable transduction by retroviruses," *Mol. & Cell Biol.*, 2001, 21(4), 1164-1172.
Daniel, R., "Evidence that the retroviral DNA integration process triggers an ATR-dependent DNA damage response," *PNAS*, 2003, 100(8), 4778-4783.
de Klein, A., et al., "Targeted disruption of the cell-cycle checkpoint gene *ATR* leads to early embryonic lethality in mice," *Curr. Biol.*, 2000, 10, 479-482.
Durocher, D., et al., "DNA-PK, ATM and ATR as sensors of DNA damage: variations on a theme?," *Curr. Opin. +Cell Biol.*, 2001, 13, 225-231.
Franchitto, A., et al., "Bloom's syndrome protein is required for correct relocalization of RAD50/MRE11/NBS1 complex after replication fork arrest," *J. Cell Biol.*, 2002, 157(1), 19-30.
Gaken, J.A., et al., "Efficient retroviral infection of mammalian cells is blocked by inhibition of poly(ADP-ribose) polymerase activity," *J. of Virology*, 1996, 70(6), 3992-4000.
Hall-Jackson, CA., et al., "ATR is a caffeine-sensitive, DNA-activated protein kinase with a substrate specificity distinct from DNA-PK," *Oncogene*, 1999, 18, 6707-6713.
Katz, R.A., et al., "The retroviral enzymes," *Ann. Rev. Biochem.*, 1994, 63, 133-173.
Katz, R.A., et al., "Role of DNA end distortion in catalysis by avian sarcoma virus integrase," *J. Biol. Chem.*, 2001, 276(36), 34213-34220.

(Continued)

*Primary Examiner*—Larry R Helms
*Assistant Examiner*—Agnieszka Boesen
(74) *Attorney, Agent, or Firm*—Drinker Biddle & Reath LLP

(57) ABSTRACT

Cellular targets for anti-retroviral drug development are disclosed. The cellular targets comprise ATR kinase and its relevant substrates, based on the identification of the ATR kinase as required for the final step of retroviral DNA integration. Assays for identifying modulators of retroviral integration via the ATR kinase pathway are disclosed, as well as modulators identified by such assays. Pharmaceutical preparations and methods of their use in treating retroviral infection are also disclosed.

8 Claims, 19 Drawing Sheets

OTHER PUBLICATIONS

Lakin, N.D., et al., "The ataxia-telangiectasia related protein ATR mediates DNA-dependent phosphorylation of p53," *Oncogene*, 1999, 18, 3989-3995.

Liu, Q., et al., "Chk1 is an essential kinase that is regulated by Atr and required for the $G_2/M$ DNA damage checkpoint," *Genes & Dev.*, 2000, 14, 1448-1459.

Naldini, L., et al., "In vivo gene delivery and stable transduction of nondividing cells by a lentiviral vector," *Science*, 1996, 272, 263-267.

Nunnari, G., et al., "Residual HIV-1 disease in seminal cells of HIV-1-infected men on suppressive HAART: latency without ongoing cellular infections," *Aids*, 2002, 16, 39-45.

Ohnishi, A., et al., "Differential pharmacokinetics of theophylline in elderly patients," *Drugs Aging*, 2003, 20(1), 71-84.

Orlando, V., "Mapping chromosomal proteins in vivo, by formaldehyde-crosslinked-chromatin immunoprecipitation," *TIBS*, 2000, 25, 99-104.

Otero, M., et al., "Peripheral blood dendritic cells are not a major reservoir for HIV type 1 in infected individuals on virally suppressive HAART," *AIDS Res. & Hum. Retroviruses*, 2003, 19(12), 1097-1103.

Patel, C.A., et al., "Human immunodeficiency virus type 1 Vpr induces apoptosis in human neuronal cells," *J. Virol*, 2000, 74(20), 9717-9726.

Patel, C.A., et al., "Lentiviral expression of HIV-1 Vpr induces apoptosis in human neurons," *J. Neurovirol*, 2002, 8, 86-99.

Pleasure, S.J., et al., "NTera 2 cells: a human cell line which displays characteristics expected of a human committed neuronal progenitor cell," *J. Neurosci. Res.*, 1993, 35, 585-602.

Pleasure, S.J., et al., "Pure, postmitotic, polarized human neurons derived from NTera 2 cells provide a system for expressing exogenous proteins in terminally differentiated neurons," *J. Neurosci*, 1992, 12(5), 1802-1815.

Pommier, Y., et al., "Inhibitors of human immunodeficiency virus integrase," *Adv. In Virus Res.*, 1999, 52, 427-458.

Post, S., et al., "Phosphorylation of serines 635 and 645 of human Rad17 in cell cycle regulated and is required for $G_1/S$ checkpoint activation in response to DNA damage," *Proc. Natl. Acad. Sci. USA*, 2001, 98(23), 13102-13107.

Sarkaria, J.N., et al., "Inhibition of ATM and ATR kinase activities by the radiosensitizing," *Cancer Res.*, 1999, 59, 4375-4382.

Sarkaria, J.N., et al., "ATM as a target for novel radiosensitizers," *Semin. Radiat. Oncol.*, 2001, 11(4), 316-327.

Shiloh, Y., "ATM and ATR: networking cellular responses to DNA damage," *Curr. Opin. In Genet. & Devel.*, 2001, 11,71-77.

Takase, K., et al., "Reversible $G_1$ arrest induced by dimethyl sulfoxide in human lymphoid cell lines: kinetics of the arrest and expression of the cell cycle marker proliferating cell nuclear antigen in Raji cells," *Cell Growth & Differ*, 1992, 3, 515-521.

Take, Y., et al., "OK-1035, a selective inhibitor of DNA-dependent protein kinase," *Biochem. & Biophys. Res. Comm.*, 1995, 215(1), 41-47.

Tibbetts, R.S., et al., "A role for ATR in the DNA damage-induced phosphorylation of p53," *Genes & Dev.*, 1999, 13, 152-157.

Tibbetts, R.S., et al., "Functional interactions BRCA1 and the checkpoint kinase ATR during genotoxic stress," *Genes & Dev.*, 2000, 14, 2989-3002.

Wang, T.G., et al., "In vitro cellular tropism of human T cell leukemia virus type 2," *AIDS Res. & Hum. Retroviruses*, 2000, 16(16), 1661-1668.

Ward, I.M., et al., "Histone H2AX is phosphorylated in an ATR-dependent manner in response to replicational stress," *J. Of Biol. Chem.*, 2001, 276(51), 47759-47762.

Yoder, K.E., et al., "Repair of gaps in retroviral DNA integration intermediates," *J. of Virol.*, 2000, 74(23), 11191-11200.

Zhou, B.-B. S., et al., "Caffeine abolishes the mammalian $G_2/M$ DNA damage checkpoint by inhibiting ataxia-telangiectasia-mutated kinase activity," *J. Biol. of Chem.*, 2000, 275(14), 10342-10348.

Zhou, B.-B.S., et al., "The DNA damage response: putting checkpoints in perspective," *Nature*, 2000, 408, 433-439.

Zhu, K., et al., "Irreversible inhibition of human immunodeficiency virus type 1 integrase by dicaffeoylquinic acids," *J. of Virol.*, 1999, 73(4), 3309-3316.

Zou, L., et al., "Regulation of ATR substrate selection by Rad17-dependent loading of Rad9 complexes onto chromatin," *Genes & Dev.*, 2002, 16, 198-208.

\* cited by examiner

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 1
```

```
tcagcgatag tcgtaactca gcat                                          24

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 2
agccgtggcc caatgat                                                  17

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
ccgtgttaca tcggttgctg cacaa                                         25

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
accaatgtgg tgaatggtca a                                             21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
ctacgagcac ctgcatgaag c                                             21

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 6
gcctcccaaa gtgctgggat tacag                                         25

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 7
ggcttcggtt gtacgcggtt aggagt                                        26

<210> SEQ ID NO 8
<211> LENGTH: 20
<212> TYPE: DNA
<213> ORGANISM: Artificial Sequence
```

<220> FEATURE:
<223> OTHER INFORMATION: Oligonucleotide primer

<400> SEQUENCE: 8
aggtgcacac caatgtggtg					20

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 9
aaaagcaccg tgcatgc					17

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 10
caaatggcgt ttattgtatc g					21

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
gattggtgga agtaaggtgg					20

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 12
agctccaggg cccggagcga c					21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 13
cttcaatgcc cccaaaacca a					21

<210> SEQ ID NO 14
<211> LENGTH: 21
<212> TYPE: DNA
<213> ORGANISM: Artificial
<220> FEATURE:
<223> OTHER INFORMATION: Oligonucleotide primer

<400> SEQUENCE: 14
gtaactagag ataccctcaa c					21

```
-continued

<210> SEQ ID NO 15
<211> LENGTH: 21
<212> TYPE: DNA
<213> ORGANISM: Artificial
<220> FEATURE:
<223> OTHER INFORMATION: Oligonucleotide primer

<400> SEQUENCE: 15
cagatctggt ctaaccagag a                                              21

<210> SEQ ID NO 16
<211> LENGTH: 23
<212> TYPE: DNA
<213> ORGANISM: Artificial
<220> FEATURE:
<223> OTHER INFORMATION: Oligonucleotide primer

<400> SEQUENCE: 16
agtggcgagc cctcagatgc tgc                                            23
```

US 7,736,848 B2

CELLULAR TARGETS FOR TREATMENT OF RETROVIRAL INFECTION

CROSS REFERENCE TO RELATED APPLICATIONS

This is a continuation-in-part of PCT Application No. PCT/US03/31164, filed Sep. 30, 2003, which claims benefit of U.S. Provisional Patent Application No. 60/414,791, filed Sep. 30, 2002, the disclosures of which are hereby incorporated by reference herein in their entireties.

GOVERNMENT SUPPORT

Pursuant to 35 U.S.C. §202(c), it is acknowledged that the United States government may have certain rights in the invention described herein, which was made in part with funds from the National Institutes of Health, Grant Nos. AI40385, CA71515, CA06927, and CA98090.

FIELD OF THE INVENTION

This invention relates to the field of retroviruses and pathological conditions caused by retroviruses. In particular, this invention provides novel cellular targets for anti-retroviral drug development.

BACKGROUND OF THE INVENTION

Retroviruses cause several diseases and pathological conditions, including a variety of tumors and leukemias. For instance, human immunodeficiency virus (HIV) is the causative agent of acquired immunodeficiency syndrome (AIDS) in humans. Another significant disorder, adult T-cell leukemia-lymphoma, is caused by the retrovirus HTLV I (human t-cell leukemia virus type I). HTLV I also has been associated with other diseases, such as tropical spastic paraparesis and HTLV I-associated myelopathy. Moreover, many animal diseases of agricultural and veterinary importance are known to be caused by retroviruses. These include avian sarcoma leukosis virus (ASLV), feline leukemia virus (FeLV), bovine immunodeficiency virus (BIV) and equine infectious anemia virus (EIAV), among others.

Retroviruses encode several enzymes that are assembled into the virus particle and whose activities catalyze essential steps in the infectious cycle: (a) protease (PR), (b) the polymerase and (c) ribonuclease H(RNAse H) activities of reverse transcriptase (RT), and (d) integrase (IN). Following attachment and penetration of the retrovirus into the host cell, the RT activities catalyze reverse transcription of the viral RNA into DNA, and IN catalyzes the integration of the retroviral DNA into the host cell DNA. The cellular transcription and translation machinery is used to produce viral RNA from the integrated viral DNA and thereafter to produce the viral proteins.

Retroviral DNA integration proceeds in three distinct steps, the first two of which have been reconstituted in vitro with the purified retroviral enzyme, integrase. In the first step of integration, denoted processing, retroviral integrase removes two nucleotides from 3'-ends of the viral DNA. In the second step, joining, these newly created ends are joined to staggered phosphates in the host DNA in a concerted cleavage and ligation reaction. This process creates an integration intermediate that leaves gaps in the flanking host DNA sequence (FIG. 1). In the last step of integration, these gaps are repaired, creating a stably integrated provirus. This repair reaction can also be reconstituted in vitro using combinations of various polymerases, ligases, and an endonuclease (Brin et al., J. Biol. Chem. 275: 39287-39295, 2000; Yoder & Bushman, J. Virol. 74: 11191-11200, 2000), but the identity and mechanism of action of proteins responsible for these reactions in vivo are not yet known. Retroviral DNA integration is an essential step in retroviral replication and the integrase protein is an attractive target for antiviral therapy. However, the integrase gene is virus-encoded and therefore subject to a high mutation rate, leading to drug resistance. This rapid evolution of resistance should not occur with drugs that target cellular functions necessary for integration, but not cell viability.

As reported in WO 00/17386 and by Daniel et al. (Science 284: 644-647), retroviral infection induces programmed death in scid lymphocytes that are deficient in the DNA repair protein, DNA-PK (DNA-dependent protein kinase). Furthermore, this response to infection requires an active integrase. In addition to retrovirus-induced scid cell death, it was also observed that stable transduction by retroviral vectors, a measure of successful DNA integration, is reduced in cells deficient in DNA-PK and other components of the non-homologous end-joining (NHEJ) pathway. These findings indicate that retroviral DNA integration is sensed as DNA damage by the host cell, and that DNA repair proteins, such as DNA-PK, may be recruited to facilitate stable integration into the host genome. Components of the DNA damage response pathway(s) that are required for this process therefore present advantageous targets for anti-retroviral therapy.

DNA-PK belongs to a family of large, PI-3K-related protein kinases, that also includes ATM (ataxia telangiectasia mutated) and ATR (ATM and Rad3 related) kinases. The ATM and ATR kinases seem to have a broader role than DNA-PK in response to DNA damage, including regulation of cell cycle checkpoints. Detection of aberrant DNA and chromosome structures by these proteins coordinately triggers checkpoint pathways and DNA repair systems (Zhou & Elledge, Nature 408: 433-439, 2000). Activation of a DNA damage checkpoint results in cell cycle arrest, allowing time for DNA repair or, in its absence, cell death.

Cells derived from A-T patients and from atm –/– knockout mice display sensitivity to ionizing radiation, chromosomal instability, and defects in cell cycle checkpoints. The regulation of checkpoints by ATM has been studied extensively and a number of ATM substrates have been identified (Shiloh, Curr. Opin. Genet. Devel. 11: 71-77, 2001; Durocher & Jackson, Curr. Opin. Cell Biol. 13: 225-231, 2001). ATM also appears to play a direct role in DNA repair at the sites of DNA damage (Durocher & Jackson, 2001, supra). This ATM function may be mediated by modification of repair proteins, such as phosphorylation of BRCA1, which is induced by ionizing radiation (Cortez et al., Science 286: 1162-1166, 1999).

Studies with an inducible, transdominant-negative ATR mutant have also implicated the ATR protein in cell cycle checkpoint control (Cliby et al., EMBO J. 17: 159-169, 1998). Furthermore ATR, like ATM, can respond to DNA damage induced by ionizing radiation, and some data suggest that phosphorylation is sequential, with ATM kinase being activated first (Durocher & Jackson, 2001, supra). ATR and ATM seem therefore to be operating in similar or overlapping pathways (Shiloh et al., 2001, supra). However, the kinase activities of these proteins also have distinct functions—for example, BRCA1 is phosphorylated by ATR, but not ATM, in response to damage induced by UV light and stalled DNA replication forks (Tibbetts et al., Genes Dev. 14: 2989-3002, 2000).

In addition to phosphorylation of checkpoint and DNA repair proteins, ATM and ATR also share in vitro and in vivo sensitivity to the radiosensitizing agent caffeine (Zhou et al., J. Biol. Chem. 275: 10342-10348, 2000; Blasina et al., Curr. Biol. 9: 1135-1138, 1999; Hall-Jackson et al., Oncogene 18: 6707-6713, 1999). The IC50s for ATM and ATR kinase inhibition are similar, and fall in the range of 1-2 mM in vitro (Sarkaria et al., Cancer Res. 59: 4375-4382, 1999). Although ATM function is required for the residual retroviral transduction that occurs in cells that are deficient in NHEJ proteins such as DNA-PK, retroviral transduction is normal in ATM-deficient cells (WO 00/17386; Daniel et al., Mol. Cell. Biol. 21: 1164-1172, 2001). Further, DNA-PK is not sensitive to caffeine (Sarkaria et al., 1999, supra).

SUMMARY OF THE INVENTION

It has been discovered in accordance with the present invention that the cellular ATR kinase is required for efficient retroviral integration. Accordingly, the present invention features both in vitro and in vivo methods of identifying agents that modulate this novel cellular target for retroviral therapy, and resultant agents identified by such methods. Such in vitro methods comprise combining a test compound suspected of inhibiting production or activity of ATR kinase with ATR kinase and a downstream target of ATR kinase activity, and then measuring the effect of the test compound on the product of ATR kinase reactivity with the downstream target as compared to appropriate controls. Such in vivo methods comprise combining a test compound suspected of inhibiting production or activity or ATR kinase with cultured transducible host cells and a retroviral vector encoding a detectable gene product under conditions wherein transduction of the host cells with the retroviral vector results in production of the detectable gene products, and then measuring the amount of detectable gene product produced as compared to appropriate controls.

The invention also features a method of inhibiting retroviral replication in a host cell, which comprises inhibiting the production or activity of cellular ATR kinase or downstream targets of ATR kinase. The invention also provides pharmaceutical preparations for treating retroviral infection, which utilize as their active ingredient agents that modulate ATR kinase or downstream targets of ATR kinase. Such agents include methylxanthines such as caffeine, paraxanthine, theobromine, and theophylline, as well as their respective derivatives and metabolites. The invention further provides methods of inhibiting retroviral infection in subjects infected with a retrovirus comprising administering the pharmaceutical preparations of the invention to the subjects in an amount and for a time effective for inhibiting retroviral replication.

Various features and advantages of the present invention will be understood by reference to the drawings, detailed description and examples that follow.

<0.01); black columns, cells infected with 10-3 dilution of the virus. (B) ATRkd protein detected after treatment of GM847/ATRkd cells with 1 or 5 μg/ml doxycycline for 24 hr. Cells were harvested and Western blot analysis was performed with an ATR antibody. (C) Growth of cells expressing ATRkd. GM847/ATRkd cells were plated at a density of $10^5$ cells per 60 mm dish in the presence of doxycycline, which was left on the cells for 48 hr and then removed. At indicated intervals, cells were harvested and viable cells counted. Open circles, cells grown in the absence of doxycycline; crosses, cells treated with 1 μg/ml doxycycline; squares, cells treated with 5 μg/ml doxycycline. (D) Integration of ASV DNA in cells expressing ATRkd. Detection of host-viral junction DNA in cells that overexpress ATRkd. GM847/ATR-Kd cells were treated with doxycycline and infected with the ASV vector. Alu-PCR was performed 24 hr postinfection. NP, no Alu primer in the first round of PCR (cells infected in the absence of doxycycline); UN, no virus (uninfected cells).

Figure 7:
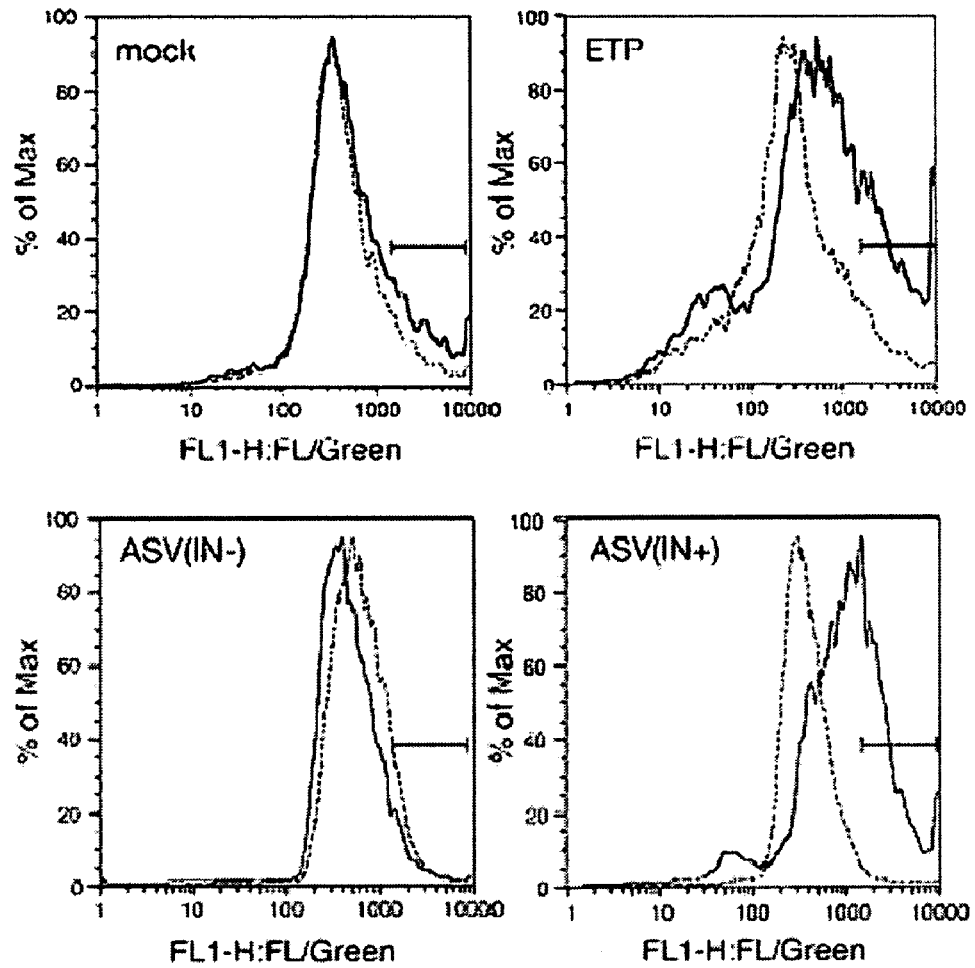

FIG. 7. Induction of apoptosis by retroviral infection of cells induced to over-express ATRkd. Doxycycline was added or not to GM847/ATRkd cells, and the following day the cells were infected at multiplicity of infection (moi) 10 with either avian sarcoma virus (ASV) vector (IN+) or the integrase-deficient (IN−) vector, or treated with 50 μM etoposide (ETP), in the continued presence or absence of doxycycline. Twenty-four hours later, cells were stained using the TUNEL assay, and analyzed as described in Experimental Methods, infra. The percentage of cells that fell within the apoptotic window is indicated. Solid lines show results with cells treated with doxycycline, dashed lines are results with uninduced cells. The bracket in each plot shows the apoptotic fraction used for the percentages shown in Table 2.

Figure 8A:
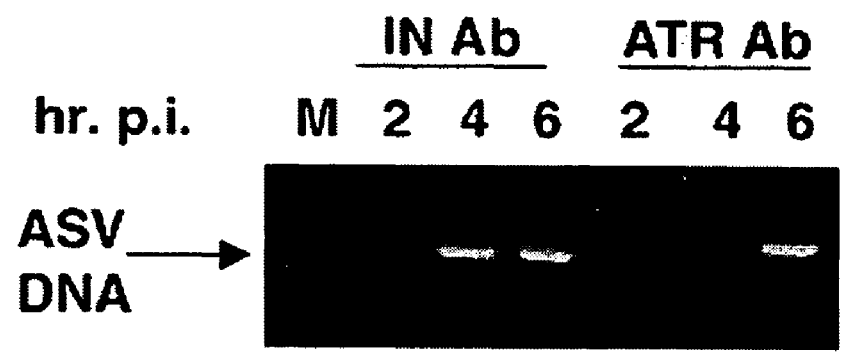
Figure 8B:
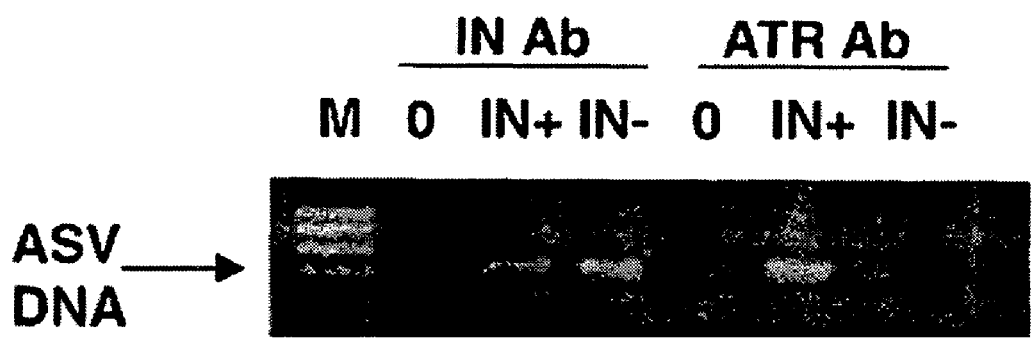

FIG. 8. Association of ASV IN and Atr with viral DNA. HeLa cells were infected and chromatin prepared at the indicated times (A) or at 6 hours (B) post-infection (pi). In (B) chromatin from cells infected with IN+ the IN− (D64E) mutant was analyzed. 0=no virus. Chromatin immunoprecipitation was performed using antibodies (Ab) against ASV IN or ATR. Viral DNA was detected using nested PCR with primers targeting viral LTR sequences.

Figure 9:
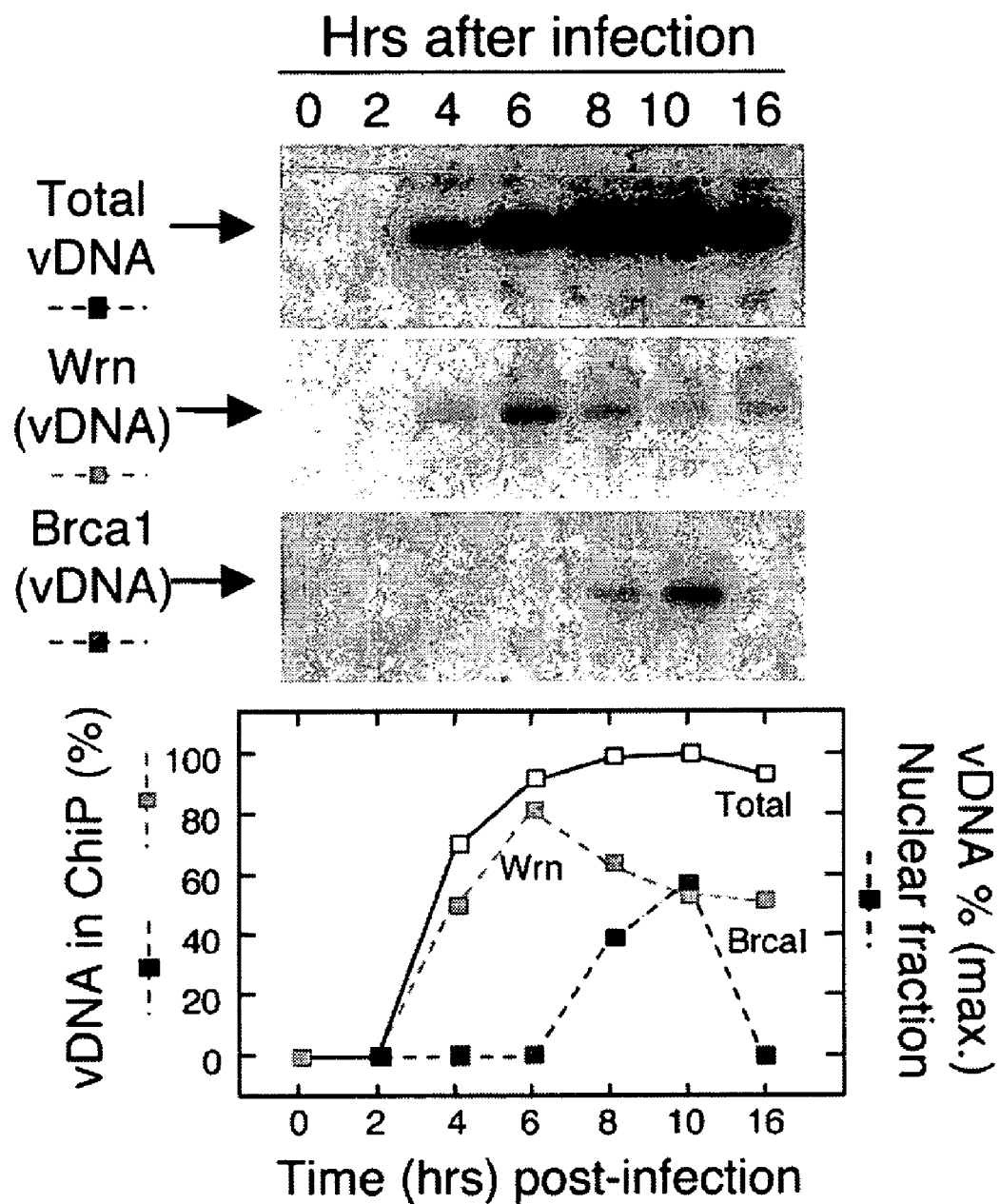

FIG. 9. Chromatin immunoprecipitation (ChIP) analysis using antibodies specific for human Wrn and Brca1 proteins. The graph shows the percentage of viral DNA that is associated with each ChIP, corrected for the immunoprecipitation efficiency of each antibody.

FIG. 10. Effect of caffeine on HIV-1 transduction of nocodazole-arrested cells. (A) Exponentially dividing 293T cells were infected with the same aliquots of HIV-1-based vectors and exposed to the indicated concentrations of caffeine for 24 h. Two days post infection, cells were stained in a β-galactosidase assay and blue cells were counted. (B) 293T cells were infected and treated with caffeine as in (A), except they were arrested with nocodazole 24 hrs prior to addition of the vectors. (C) Amount of PCNA in dividing and nocodazole-treated 293T cells. Cells were treated with nocodazole as in (B), for 24 hrs, at which time they were harvested and Western blot analysis was performed. (D) Ser 10-phosphorylated histone H3 in dividing and nocodazole-treated cells. "wt"—HIV-1-based vector containing Vpr and wild-type integrase, MAV—multiply attenuated HIV-1-based vector, IN−—HIV-1-based vector carrying a D64V substitution in retroviral integrase.

FIG. 11. Effect of caffeine on transduction of contact-inhibited MEFs. (A) Exponentially dividing mouse embryo fibroblasts were infected with the HIV-1-base vector carrying Vpr and exposed to caffeine for 24 hrs. Two days post-infection, cells were stained with a β-galactosidase assay and blue cells were counted. (B) MEFs were distributed in 96-well plates as in (A) and infected at the point of confluency. Caffeine was added as in (A). (C) PCNA in dividing and confluent MEFs. Cells were treated as in (A) and (B) and Western blot analysis was performed at the time when MEFs would be infected. (D) Ser 10-phosphorylated histone H3 in dividing and confluent MEFs.

FIG. 12. Effect of caffeine on transduction of terminally differentiated neurons and macrophages. (A) Terminally differentiated hNT-2 neurons were infected with the HIV-1-based vector carrying Vpr and exposed to caffeine for 24 hrs. Two days post-infection, cells were stained in a α-galactosidase assay and blue cells were counted. (B) PCNA in terminally differentiated neurons. Cells were treated as in (A) and Western blot analysis was performed at the time when cells would be infected, with $2\times10^5$ cells per lane. (C) Effect of caffeine on transduction of terminally differentiated macrophages. Terminally differentiated macrophages were infected with the HIV-1-based vector and exposed to caffeine for 24 h. Two days post-infection, cells were stained in a β-galactosidase assay and blue cells were counted.

FIG. 13. Effect of overexpression of dominant negative, kinase-dead ATRkd protein on transduction of nocodazole-arrested cells. (A) Exponentially dividing GM847/ATRkd cells were exposed to doxycycline and infected with the HIV-1-based vectors. Two days post-infection, cells were stained with a β-galactosidase assay and blue cells were counted. (B) GM847/ATRkd cells were infected and doxycycline-treated as in (A), except they were growth arrested with nocodazole 24 hrs prior to addition of the viruses. (C) PCNA in dividing and nocodazole-treated GM847/ATRkd cells. Cells were treated as in (A) and Western blot analysis was performed at the time when cells would be infected. (D) Ser 10-phosphorylated histone H3 in dividing and nocodazole-treated GM847/ATRkd cells. "wt"—HIV-1-based vector containing Vpr protein and wild-type integrase, MAV—multiply attenuated HIV-1-based vector, IN−—HIV-1-based vector carrying a D64V substitution in retroviral integrase.

Figure 14A:
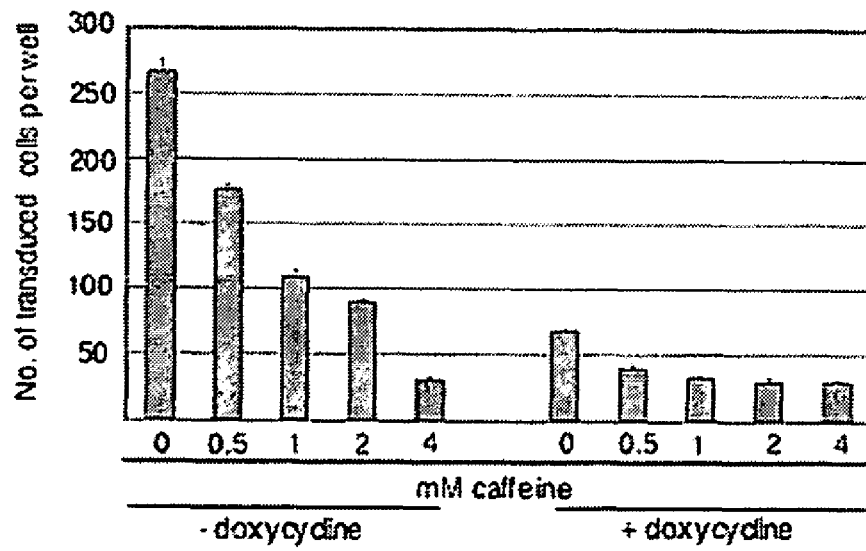
Figure 14B:
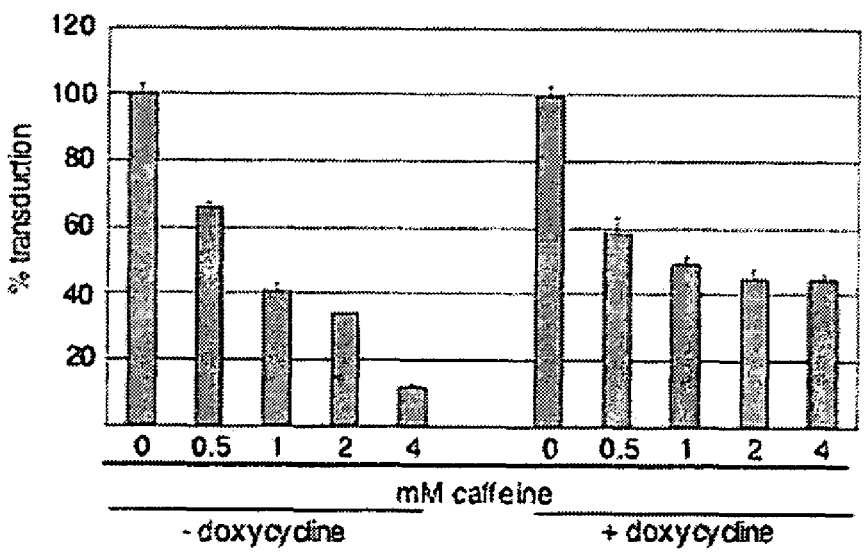

FIG. 14. Effect of caffeine on HIV-1 transduction of ATR-deficient cells. (A) Exponentially dividing GM847/ATRkd cells were exposed to doxycycline (5 μg/ml), infected with the same aliquots of HIV-1-based vectors and treated with the indicated concentrations of caffeine. Two days post-infection, cells were stained in a β-galactosidase assay and transduced cells were counted. (B) Caffeine effect expressed as relative transduction efficiency. 100%-number of transduced cells in absence of caffeine, irrespective of the presence or absence of doxycycline.

Figure 15A:
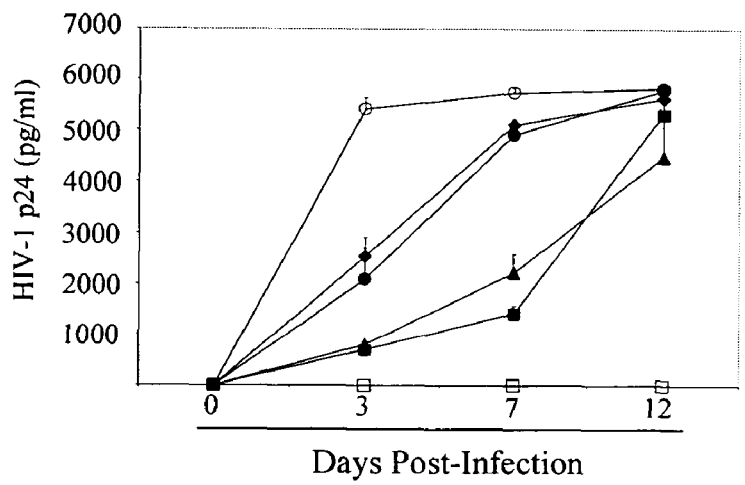
Figure 15B:
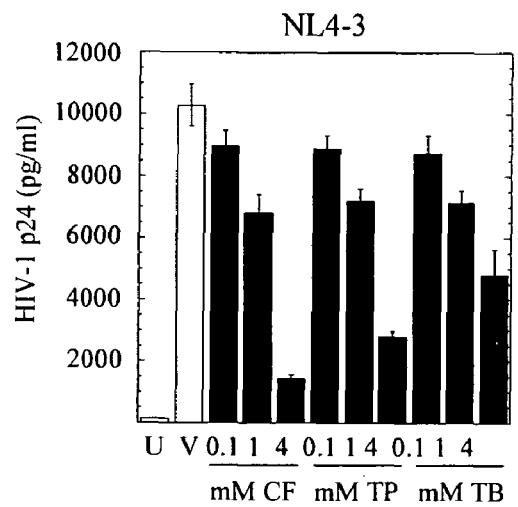
Figure 15C:
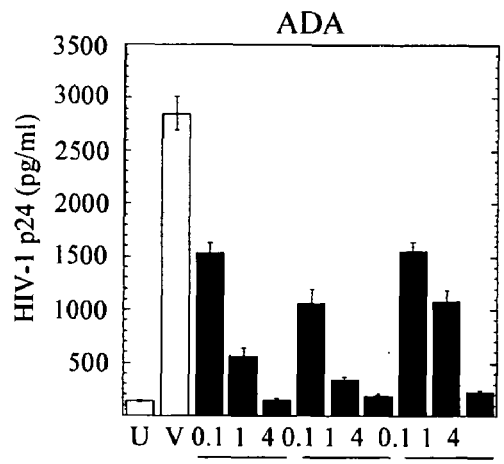

FIG. 15. Caffeine and related methylxanthines suppress replication by HIV-1 NL4-3 and ADA strains. (FIG. 15A) Peripheral blood mononuclear cells (PBMCs) were infected with the HIV-1 strain NL4-3 and treated with methylxanthines (4 mM concentration). The level of p24 antigen in the culture supernatant was measured at 3, 7 and 12 days post-infection. Open circles—culture infected with the NL4-3 virus in the absence of methylxanthines, open squares—uninfected cells, filled diamonds—culture infected with NL4-3 and treated with theobromine, filled circles—culture infected with NL4-3 and treated with paraxanthine, filled triangles—culture infected with NL4-3 and treated with caffeine, filled squares—culture infected with NL4-3 and treated with theophylline. PBMCs were infected with the NL4-3 (FIG. 15B) and ADA (FIG. 15C) strains and treated with methylxanthines. The level of HIV-1 p24 antigen in the culture supernatant was measured at 6 days post-infection. FIG. 15B—NL4-3-infected culture, FIG. 15C—ADA-infected culture. CF—cells infected with a given HIV-1 strain and treated with caffeine, TP—cells infected with a specific HIV-1 strain and treated with theophylline, TB—cells infected with a specific HIV-1 strain and treated with theobromine, V—cells infected with a specific HIV-1 strain, no methylxanthine added, U—uninfected cells. Black columns—a methylxanthine was added to culture, white columns—no methylxanthine was added.

FIG. 16. Effect of caffeine on early steps of the HIV-1 life-cycle. PBMCs were infected with the NL4-3 strain and treated with methylxanthines. Twenty-four hours post-infection, cells were harvested and analyzed. The relative intensity of bands was determined by Phosphoimager and densitometry analysis and compared to the intensity of sample infected with the NL4-3 virus, but untreated with any of the methylxanthines (left panels). (A) Level of gag HIV-1-specific DNA in infected and methylxanthine-treated cultures. (B) Level of HIV-1 2-LTR DNA circles. (C) Level of viral-host DNA joining as evaluated by Alu-PCR. (D) Level of gag HIV-1 RNA. (E) Control comparison of beta-globin DNA level in analyzed cells. CF—cells infected with NL4-3 and treated with caffeine, TP—cells infected with NL4-3 and treated with theophylline, TB—cells infected with NL4-3 and treated with theobromine, PX—cells infected with NL4-3 and treated with paraxanthine, V—cells infected with NL4-3, no methylxanthine added, U—uninfected cells, AC—ACH-2 cells, NA—ACH-2 cells, no Alu primer in the first round of PCR.

FIG. 17. Effects of caffeine on late steps of the HIV-1 life-cycle. ACH-2-cells were stimulated with PMA or left unstimulated, and treated with methylxanthines at given concentrations. Twenty-four hours after addition of PMA and methylxanthines, cultures and cells were analyzed. (A) HIV-1 p24 antigen level in the culture supernatant. (B) Intracellular HIV-1 p24 antigen level. M—mock, no methylxanthine was added, CF—caffeine-treated cells, TP—theophylline-treated cells.

Figure 18:
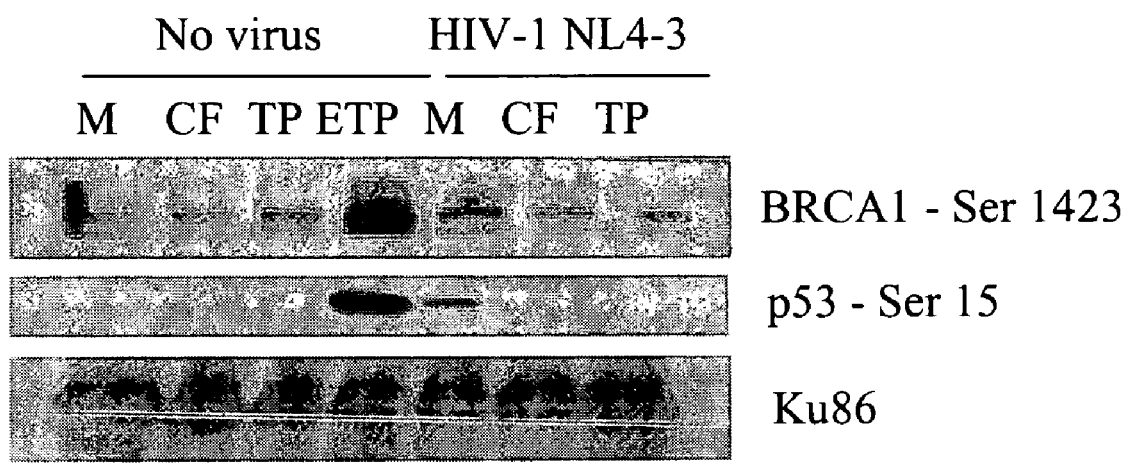

FIG. 18. Caffeine suppresses ATR— and ATM-mediated phosphorylation. PBMCs were infected with the NL4-3 virus and treated with caffeine and theophylline, and harvested 24 hrs later. Cell lysates were subjected to Western blotting analysis to detect the BRCA1 phosphorylated on serine 1423 and the p53 protein phosphorylated on serine 15. The level of Ku 86 protein served as a loading control. M—mock, no methylxanthine added, CF—caffeine-treated cells, TP—theophylline-treated cells.

DETAILED DESCRIPTION OF ILLUSTRATIVE EMBODIMENTS

The present invention features assays, active agents, pharmaceutical preparations and methods of treating retroviral infection, arising from the inventors' identification of ATR kinase as an integral component of the retroviral lifecycle, required for stable retroviral DNA integration into a host genome. Without intending to be limited by any mechanism as to how ATR kinase is involved in retroviral integration, the inventors offer the following discussion related to the role of ATR kinase in the retroviral lifecycle.

As described in detail in the examples below, the inventors have shown that methylxanthines such as caffeine inhibit stable transduction by HIV-1- and ASV-based retroviral vectors at doses that have little or no effect on early steps that precede integration, the synthesis of viral DNA and its nuclear import. In addition, methylxanthines do not inhibit integrase activities in vitro and have no effect on LTR-driven expression of a selectable reporter gene in vivo. However, methylxanthines inhibit stable retroviral DNA integration, as evaluated by Alu-PCR. It has now been demonstrated that the ATR kinase, a major target of methylxanthines such as caffeine, is required for stable retroviral DNA integration and transduction, whereas absence or inhibition of the related kinases, ATM and mTOR has no effect on transduction efficiency under the conditions tested.

ATR is a major component in cellular DNA repair. Its kinase activity is required in cellular response to ionizing and UV radiation, and collapsed replication forks. The finding that retroviral DNA integration can be inhibited by caffeine and other methylxanthines, and requires ATR, points to ATR as an advantageous cellular target for anti-retroviral therapy. One feature such an approach should be that the inhibition of cellular proteins does not have a detrimental effect on cellular function. As the observed inhibition of integration occurs at drug concentrations below those that affect growth of cultured cells, it is believed that inhibitors of ATR or other components of the DNA damage response can also serve as inhibitors of retroviral infection.

Figure 1:
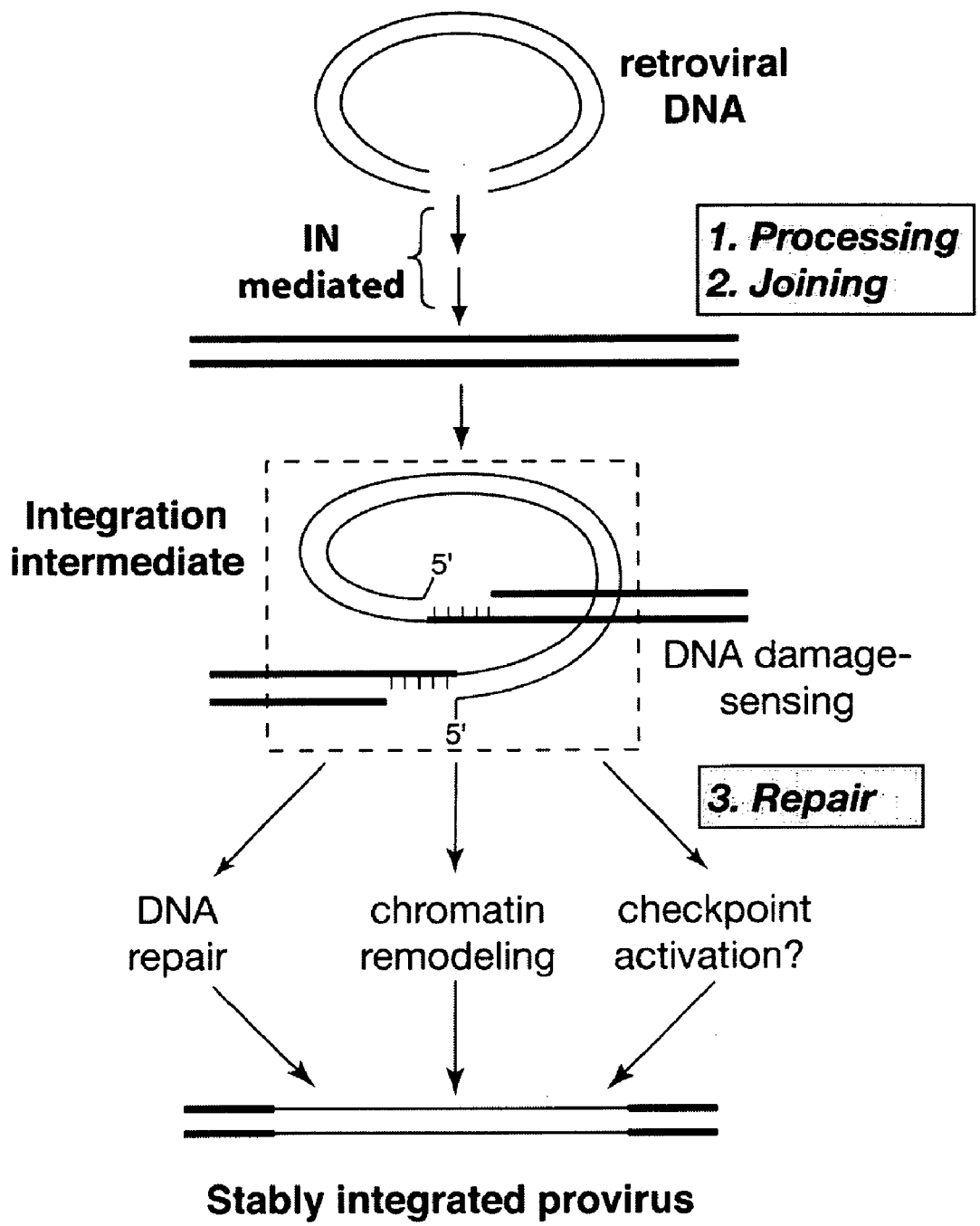
FIG. 1. Diagram showing steps in the pathway of stable retroviral DNA integration.

What aspect of retroviral DNA integration requires the ATR function? The product of the first two steps of retroviral DNA integration is an intermediate comprising the viral DNA flanked by gaps in host DNA sequence (FIG. 1). These DNA gaps, and perhaps discontinuities in the viral DNA, need to be repaired to create a stable integrated provirus. Furthermore, unrepaired gaps might become double-strand breaks when a cellular replication fork encounters such a lesion. On the basis on comparisons of experimental data with computer simulations, it is believed that this, or a related event, triggers the apoptotic response in NHEJ-deficient scid lymphocytes (Katz et al., J. Biol. Chem. 276: 34213-34220, 2001). In this context, integration-incurred damage may be similar to other replication fork catastrophes in which ATR has been proposed to play a pivotal role (Tibbetts et al., 2000, supra). Without being bound to any particular theory or mechanism of action, it may be that signaling through ATR-mediated phosphorylation of various targets leads to a transient cell cycle arrest, and recruitment or activation of the proteins necessary for repair. Failure in either or both processes could therefore render the integration intermediate unstable and could also lead to cell death. In this model, the observed reduction in integration efficiency may reflect the loss of infected cells from the population. However, as discussed herein, HIV-1 transduction is effectively reduced in non-dividing cells as well as dividing cells. For this reason, it may be that ATR kinase is directly involved in postintegration repair at sites of retroviral DNA integration, through either recruitment or modification of the necessary nucleic acid repair proteins.

Thus, the present invention features ATR kinase as a novel cellular target for inhibition of retroviral replication. Though all retroviral replication may be targeted in this manner, of particular interest is the inhibition of HIV replication, as a new therapy for A/DS. Current anti-HIV therapies target HIV proteins, predominantly HIV reverse transcriptase and protease. However, rapid emergence of resistance to these drugs is well documented, due to the ability of the virus to rapidly mutate. ATR kinases are encoded by a cellular gene, which does not mutate with the frequency of HIV or any other retrovirus. Accordingly, inhibitors of ATR kinase could impede or interrupt retroviral replication, and the probability of resistance developing to such inhibitors would be comparatively low as compared to inhibitors of viral genes. Moreover, the effect of ATR kinase on retroviral DNA integration can be inhibited under conditions that do not result in significant inhibition of cell viability, as demonstrated by studies on the ATR kinase inhibitor, caffeine. This enables the option of delivering an ATR inhibitor systemically, without incurring overall cellular toxicity. Alternatively, targeting of ATR inhibitors to cells typically subject to retroviral infection may be employed.

The identification of ATR kinase as required for the final step of retroviral DNA integration also implicates one or more downstream substrates of ATR kinase in the retroviral integration process. Accordingly, compounds that modulate one or more of these downstream substrates are also considered useful in the present invention. Several substrates of ATR kinase have been identified and characterized. These include: (1) ATRIP (Guntuku et al., Science 294:1713-1716, 2001); (2) Bloom syndrome protein (Franchitto & Pichierri, J. Cell Biol. 157:19-30, 2002); (3) Rad17 (Zou et al., Genes Dev. 16:198-208, 2002; Weng et al., Proc Natl Acad Sci USA 98:13102-13107, 2001); (4) Histone H2AX (Ward & Chen, J Biol. Chem. 276:47759-47762, 2001); (5) Chk1 (Liu et al., Genes Dev. 14:1448-1459, 2000); (6) p53 (Lakin et al., Oncogene 18:3989-3995, 1999; Tibbetts et al., Genes Dev. 13:152-157, 1999; and (7) BRCA1 (Tibbetts et al., Genes Dev. 14:2989-3002, 2000). However, any downstream target of ATR kinase may be implicated in control of retroviral integration, and therefore is contemplated as a cellular target for development of anti-retroviral agents. Substrates and downstream targets of ATR kinase, whether directly or indirectly acted upon by ATR kinase, may be considered part of an ATR kinase cascade.

One aspect of this invention features screening assays for identifying compounds that inhibit retroviral replication by modulating ATR kinase or its relevant substrates. Preferably, the ATR kinase is a human ATR kinase, and the retrovirus is one that infects humans, e.g., HIV and HTLV. However, inasmuch as animal diseases of agricultural and veterinary importance are known to be caused by retroviruses (e.g., ASLV, FeLV, BIV, EIAV), other embodiments of the invention target mammalian or avian ATR kinases, for treatment of retroviral infections of agronomic and veterinary significance.

A preferred type of assay to identify modulators of ATR kinase activity is one that can measure ATR kinase activity in vitro, in the presence or absence of a test compound suspected of being able to regulate ATR activity. For instance, one of skill in the art would appreciate that a cell-free ATR kinase activity assay could be utilized, combining ATR with one of its phosphorylation substrates, e.g., BRCA1, and measuring incorporation of labeled phosphate into the substrate. Alternatively or in addition, assays of more relevance to retroviral integration may be utilized. For example, as described in the examples to follow and in the art (e.g., Daniel et al., 1999, supra; WO 00/17386), stable transduction of cultured cells by a retroviral-based vector expressing a detectable gene product may be used to assess retroviral integration in the presence or absence of a test compound suspected of regulating ATR kinase activity or the activity of one of its substrates that may be involved in the integration process. Detectable gene products include, but are not limited to, Beta-galactosidase, placental alkaline phosphatase, secreted embryonic alkaline phosphatase, luciferase, chloramphenicol acetyltransferase, Beta-glucuronidase, green fluorescent protein, red fluorescent protein, yellow fluorescent protein, cyan fluorescent protein, or cerianthus orange fluorescent protein. Detectable gene products also include proteins that confer drug resistance, e.g., resistance to neomycin, tetracycline, hygromycin, and the like, as would be appreciated by one of skill in the art.

In a more specific assay, the integration of such vectors into genomes of cultured cells may be monitored by Alu-PCR. As a control to ensure that a test compound is affecting a cellular DNA repair enzyme rather that the retroviral integrase, integrase assays known in the art also may be carried out in the presence or absence of the test compound. As another control to focus on ATR activity in the cultured cells, assays may be performed in the presence of known inhibitors of other DNA repair enzymes. For instance, it is known that rapamycin inhibits mTOR (Sarkaria et al., 1999, supra), and DNA $PK_{CS}$ can be inhibited by single stranded DNA, pyrophosphate, 6-dimethyl-aminopurine and the pyridone derivative, OK-1035 (Take et al., Biochem. Biophys. Res. Comm. 215: 41-47, 1995).

It will be appreciated by those of skill in the art that regulation of expression of ATR kinase-encoding genes is also a means by which the kinase can be modulated in the treatment of retroviral infection. Further, as an integral component of cell cycle regulation, expression of ATR kinase genes is likely controlled by at least one transactivating protein. Accordingly, assays for agents capable of inhibiting or otherwise modulating such activation or induction of expression should identify additional useful compounds for the treatment of retroviral infection. Such assays are familiar to the skilled practitioner. Furthermore, such assays may be employed to identify compounds that modulate expression of genes encoding downstream substrates of ATR kinase.

Another aspect of the present invention features compounds identified by any of the foregoing methods. Such compounds may include, but are not limited to, antibodies and antibody fragments that bind the ATR kinase at an active site or other epitope that interferes with enzyme activity, antisense or other agents that modulate expression of genes encoding the ATR kinase, and inhibitors, antagonists, or reverse agonists of the ATR kinase, including, but not limited to, proteins, nucleic acids, or other organic molecules. Also included in this aspect of the invention are compounds identified by the above assays using downstream targets of ATR kinase as the cellular target.

Caffeine is a compound already known in the art to inhibit the ATM and ATR kinases. Moreover, as discussed herein, caffeine inhibits retroviral transduction of both dividing and non-dividing cells at concentrations that do not substantively affect cell growth. Caffeine is 1,3,7-trimethylxanthine and some of caffeine-related methylxanthines are products of caffeine metabolism in vivo (e.g., paraxanthine, theobromine and theophylline). Theophylline is in clinical use for the treatment of asthma. It has also been demonstrated that certain methylxanthines exhibit caffeine-like effects on DNA damage response (Bohm, L et al., 2003, Toxicology 193:153-160; Sarkaria, et al., 2001, Semin. Radiat. Oncol. 11: 316-327). Accordingly, another aspect of the invention comprises interfering with or inhibiting retroviral transduction or replication by using an agent that acts upon and interferes with or inhibits the ATR kinase-mediated host cell machinery needed to repair nucleic acids during retroviral DNA integration into the host cell genome. The agent may be a methylxanthine. Methylxanthines include caffeine, paraxanthine, pentoxyfylline, theobromine, theophylline, and their respective metabolites or derivatives, from whatever source derived. The agent may function in a dividing or nondividing cell. The host cell machinery may be ATR kinase or a substrate or downstream target activated directly or indirectly by ATR kinase, such as those in the ATR kinase cascade.

Also provided in accordance with the present invention are pharmaceutical preparations for treating a patient for retroviral infections. These preparations contain active ingredients that act by inhibiting the final step of retroviral integration through the modulation of ATR kinase or its downstream substrates that are required for this process. The term "patient" as used herein refers to human or animal subjects (animals being particularly useful as models for clinical efficacy of a particular composition). Selection of a suitable pharmaceutical preparation depends upon the method of administration chosen, and may be made according to protocols well known to medicinal chemists.

The pharmaceutical preparations of the invention comprising ATR kinase-modulating active agents or agents that modulate the activity of ATR substrates that affect retroviral DNA integration are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of a particular active ingredient in the chosen medium will depend on the hydrophobic or hydrophilic nature of the medium, in combination with the specific properties of the delivery vehicle and active agents disposed therein. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the compositions to be administered, its use in the pharmaceutical preparation is contemplated.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

According to another aspect of the invention, methods of treating acute or latent retroviral infection are provided, comprising administering the aforementioned pharmaceutical preparation under conditions effective to reduce or eliminate retroviral infection, or to reduce or eliminate pathological conditions associated with such infection. The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the active ingredient(s) calculated to produce the desired retroviral-inhibitory effect in association with the selected pharmaceutical carrier. Procedures for determining the appropriate dosage unit are well known to those skilled in the art. The pharmaceutical compositions may be provided to the individual by a variety of routes such as subcutaneous, topical, oral, intranasal and intramuscular.

ATR kinase-modulating compounds or agents that modulate the activity of ATR kinase substrates that affect retroviral DNA integration identified according to the methods disclosed herein may be used alone at appropriate dosages defined by routine testing in order to obtain optimal inhibition of a selected ATR kinase or its relevant substrates while minimizing any potential toxicity. In addition, co-administration or sequential administration of other anti-retroviral agents may be desirable.

The daily dosage of the products may be varied over a wide range from 0.01 to 1,000 mg per patient, per day. For oral administration, pharmaceutical preparations are preferably provided in the form of scored or un-scored tablets containing 0.01, 0.05, 0.1, 0.5, 1.0, 2.5, 5:0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages are adjusted when combined to achieve desired effects. On the other hand, dosages of these various agents may be independently optimized and combined to achieve a synergistic result wherein the pathology is reduced more than it would be if any single agent were used alone.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators of ATR kinase or its relevant substrates are typically administered in admixture with biologically compatible diluents as described above, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars, such as glucose or beta-lactose, corn sweeteners, natural and synthetic gums, such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include starch, methylcellulose, agar, bentonite, xanthan gum and the like.

For liquid forms, the active drug component can be combined in suitably flavored suspending or dispersing agents, such as the synthetic and natural gums, for example, tragacanth, acacia, methyl-cellulose and the like. Other dispersing agents that may be employed include glycerin and similar substances. For parenteral administration, sterile suspensions and solutions are desired. Isotonic preparations that generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of antibodies as individual carriers to which the compound molecules are coupled. The compounds or modulators of the present invention may also be coupled with soluble polymers as targetable drug carriers. Such polymers can include polyvinylpyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds or modulators may alternatively be administered parenterally via injection of a formulation consisting of the active ingredient dissolved in an inert liquid carrier. Injection may be either intramuscular, intra-ruminal, intratracheal, or subcutaneous. The injectable formulation consists of the active ingredient mixed with an appropriate inert liquid carrier. Acceptable liquid carriers include the vegetable oils, such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

The following examples are provided to describe the invention in greater detail. These examples are intended to illustrate, not to limit, the invention.

Example 1

Experimental Methods

The following materials and methods were employed in the examples to follow, unless otherwise described.

Cells and Viruses. GM847/ATRkd is a simian virus 40-transformed human fibroblast cell line stably transfected with a mutant ATR gene under the control of a tet-inducible promoter (Cliby, W. A., et al., (1998) EMBO J. 17, 159-169). Upon addition of doxycycline (1-5 μg/ml) the cells overproduce a protein containing a D2475A substitution that inactivates the kinase activity. HeLa, 293T, and GM847/ATRkd cells were maintained in DMEM supplemented with 10% fetal bovine serum (FBS) and Pen/Strep. The HIV-1 vector carrying the lacZ reporter was prepared as follows: 293T cells were plated on 100 mm dishes at a density approximately $10^6$ cells per dish. The following day, cells were transfected using the 3-plasmid system described previously (Naldini et al., Science 272: 263-267, 1996). 25 μg lacZ plasmid, 50 μg backbone plasmid, 5 μg VSV G plasmid were used per dish; the Profection kit (calcium phosphate) (Promega) was employed. The following day, spent medium was replaced. The second day after transfection, supernatant from the transfected 293T cells was harvested, passed through a 0.45 μM filter, and subjected to centrifugation at 4° C., 25,000 rpm, for 30 min. The virus-containing pellet was dissolved in medium. Preparation of the avian sarcoma virus (ASV) neo$^r$ vector was described previously (Daniel et al., 1999, supra). Titers of infectious units of HIV and ASV vectors were determined by transduction assays. The titer of the ASV (IN−) vector was calculated by measuring reverse transcriptase activity in viral particles and comparing the results with activity in ASV (IN+) particles of known titer. AT221JE-T cells and derivative lines were maintained as described (Daniel et al., Mol. Cell Biol. 21: 1164-1172, 2001).

Chemicals. Caffeine, theobromine, theophylline, and paraxanthine (purchased from Sigma Chemical Co.) were prepared in 100 mM stock concentrations: Caffeine was dissolved in water, whereas theobromine, theophylline, and paraxanthine were dissolved in 0.1 N NaOH. Doxycycline (Clontech) was dissolved in water at 10 mg/ml. Etoposide (ETP) was obtained from Sigma and dissolved in DMSO (stock concentration 30 mg/ml). Stocks were stored at −20° C.

Colony Assays and Cell Growth in the Presence of Caffeine and Doxycycline. To determine the effect of caffeine on cell growth, HeLa cells were plated at a density of $10^5$ cells per 60 mm dish in the presence of caffeine. The drug was kept on cells for 24 hr and then removed. At indicated intervals, cells were harvested and viable cells were counted. To determine the effect of caffeine on colony formation, 103 HeLa cells were plated on each 60 mm dish in the presence of caffeine; the drug-containing medium was removed after 24 hr and colonies counted 9 days later. To determine whether G418 treatment potentiates caffeine toxicity, G418-resistant HeLa cells were plated as above, in the presence of caffeine and 1 mg/ml G4178. Medium was replaced after 24 hr, with medium containing only G418 and colonies counted 8 days later. To determine if doxycycline treatment affects the growth of GM847/ATRkd cells, $10^5$ cells were plated per 60 mm dish in the presence of the drug. After 48 hr doxycycline-containing medium was replaced and viable cells counted at the indicated intervals.

Infection of HeLa Cells. HeLa cells were plated at 105 per 60 mm dish (FIG. 2A) and infected the following day with either the HIV-1- or ASV-based vectors for 2 hr in the presence of 10 μg/ml DEAE dextran. The virus-containing medium was then replaced with fresh medium. Two to seven days after infection with the HIV-1 vector (as indicated) cells were stained using a β-galactosidase assay (Stratagene). Cells were selected for G418 resistance one day after infection with the ASV vector by addition of 1 mg/ml G418.

Caffeine was added to cells together with the infecting virus and maintained in the medium until the following day (24 hr), at which time caffeine-containing medium was replaced with fresh medium. After infection with ASV, G418 was also added at this time.

Infection of ATR-deficient Cells. GM847/ATRkd cells were plated at 105 per 60 mm dish and infected the following day with either the HIV-1- or ASV vector for 2 hr in the presence of 10 μg/ml DEAE dextran. Doxycycline was added at the time of plating and kept on cells for 24 hr after addition of the virus. To determine the transduction efficiency of the HIV-1 vector, ATR-deficient cells were stained 48 hr post infection using a β-galactosidase assay and following the Stratagene protocol.

Infection of ATM-deficient Cells. ATM-deficient AT22IJE-T cells and AT22IJE-T cells containing a vector encoding ATM or an empty vector (Cortez et al., 1999, supra) were plated at $5 \times 10^4$ per well of a 24 well plate, 2 wells each point and infected the following day with the HIV-1 vector for 2 hr in the presence of 10 μg/ml DEAE dextran. Caffeine was added to cells together with the HIV-1 vector, and maintained in the medium until the following day (24 hr). Cells were stained three days post infection using the β-galactosidase assay.

Western Blot Analyses. For Western blot analysis of neo[r] expression, the polyclonal population of G418-resistant HeLa cells (ca. 1000 clones) was exposed to caffeine for 24 hr. Cells were then harvested, lysed, and lysates were subjected to electrophoresis in a 10% SDS polyacrylamide gel. The separated proteins were then transferred to a PVDF membrane and the filter was treated with neomycin phosphotransferase II antibody (Upstate Biotech). Bands were detected using a chemi-luminescence assay.

For detection of ATRkd, GM847/ATRkd cells were exposed to doxycycline (1 or 5 µg/ml) for 24 hr. Cells were then harvested and Western blot analysis was performed as described above, except samples were resolved by electrophoresis in a 6% SDS-polyacrylamide gel, and the filter was exposed to anti-ATR antibody (Ab-2, Oncogene Science).

Real Time PCR. Extrachromosomal DNA from infected and uninfected cells was prepared by HIRT extraction. Real-Time PCR amplification, data-acquisition and analysis were preformed with the Cephid Smart Cycler. The Biochemistry and Biotechnology Facility at the Fox Chase Cancer Center prepared the primers using BHQ-1 non-fluorogenic quencher (Biosearch Technologies). Viral sequence primers directed against ASV pol were selected using Primer Express™ (Applied Biosystems) and had the following sequences: Forward primer, 5'-TCA GCG ATA GTC GTA ACT CAG CAT-3' (SEQ ID NO:1); Reverse primer, 5'-AGC CGT GGC CCA ATG AT-3' (SEQ ID NO:2); Probe, 5'-(FAM) CC GTG TTA CAT CGG TTG CTG CAC AA (BHQ)-3' (SEQ ID NO:3). Results were normalized with those from primers against mitochondrial DNA (Asaad et al., Oncogene 19: 5788-5800, 2000). Each reaction contained 1× Reaction Buffer (20 mM Tris-HCl, pH 8.4), 50 mM KCl), 0.25 mM each dNTP, 2.5 mM $MgCl_2$, 400 nM primers, 200 nM probe and 2.5 U Platinum Taq Polymerase (Invitrogen). Relative quantitation was calculated with the Comparative Cycle Threshold Method using the untreated samples as the reference (User, B. ABI Prism 7700 Sequence Detection System; the Perkin Elmer Corporation, P/N 4303859 Rev. A. Stock No. 77802-001, 1997). This method was validated with a five-fold dilution curve of the untreated sample (slope was −0.0234). Similar results were obtained with calculations using a standard curve generated from a viral plasmid. Relative quantitation was averaged and standard deviations were determined between independent experiments.

PCR Detection of Circle Junctions In Vivo. 106 HeLa cells were plated per dish and infected the following day with 1 ml of the undiluted ASV vector (titer ca $1\times10^6$ GFU (G418-resistant colony-forming units)/ml), for 2 hr, in the presence of 10 µg/ml DEAE dextran. Caffeine-containing medium was replaced after 24 hr. Cells were harvested the following day and extrachromosomal DNA extracted using the HIRT method. DNA was dissolved in 50 µl per sample and 1-10 µl were used for PCR. Circle junctions were amplified using primers comprising ASV LTR sequences. The sequence of the upstream primer was 5'-ACC AAT GTG GTG AAT GGT CAA-3' (SEQ ID NO:4), and the sequence of the downstream was 5'-CTA CGA GCA CCT GCA TGA AGC-3' (SEQ ID NO:5). PCR was run for 45 cycles, 94° C. 30 sec, 55° C. 30 sec, and 72° C. 30 sec. PCR products were analyzed on 1.5% agarose gels.

In Vitro Assays of Integrase Activities. Reactions contained 2 µM ASV IN, 15 µM U3 18/18 substrate in 55 mM Hepes, pH 8.2, 50 mM NaCl, 2 mM 2-mercaptoethanol, 0.1% thiodiglycol, 200 µg/ml BSA, 10 µM EDTA, 4% glycerol, and 10 mM $MnCl_2$, in a final volume of 10 µl. Caffeine stocks were prepared in water, and added to the reaction as a 1/10 add, for final concentrations of 1 µM to 10 mM, as indicated. The order of additions was as follows: IN, water, 10× reaction buffer and $MnCl_2$ were combined on ice, then caffeine was added to the reactions and they were preincubated for 30 min at 30° C. Reactions were then placed on ice and the DNA substrate added. After substrate addition, the reactions were incubated at 37° C. for 15 min, and then stopped with 20 µl Maxam and Gilbert loading buffer. Samples were then analyzed by electrophoresis in a 20% sequencing gel, and the radioactive bands were detected using a Fuji Bio-Imaging Analyzer.

For HIV-1 integrase, reactions contained 1.0 M HIV IN, 1.0 µM U5 21/21 substrate (Katz & Skalka, Ann. Rev. Biochem. 63: 133-173, 1994; Coffin et al., Retroviruses, Cold Spring Harbor Laboratory, 1997) in 22 mM Hepes, pH 7.5, 5.1 mM DTT, 6% glycerol, 6.66% DMSO, 50 mM KCl and 10 mM $MnCl_2$. Conditions were as described for ASV IN, except that the final incubation time was 60 min.

Alu-PCR. HeLa cells were treated with caffeine and GM847/ATRkd cells stimulated with doxycycline as described above. Infection was performed at an m.o.i. 0.01. The inventors established first that this m.o.i. falls in the linear range for detection of viral DNA. Cells were harvested 24 hr after infection and chromosomal DNA was extracted. DNA concentrations of all samples were normalized by UV absorbance. PCR reactions (50 µL) contained 50 mM KCl, 20 mM Tris-HCl buffer (pH 8.4), 5 mM $MgCl_2$, 200 uM dNTP, 0.5 U Taq-polymerase (GibcoBRL). 100 ng of chromosomal DNA was used in the first round of PCR with Alu-primer 5'-GCC TCC CAA AGT GCT GGG ATT ACA G-3' (SEQ ID NO:6) and ASV virus primer 5'-GGC TTC GGT TGT ACG CGG TTA GGA GT-3' (SEQ ID NO:7). Samples were denatured at 92° C. for 3 min, and then subjected to 20 PCR cycles of 92° C. for 40 s, 65° C. for 40 s, and 72° C. for 1 min 30 s. Products of the first round were diluted 1/1000 and used in the 25-cycle second round (nested) with viral LTR primers: 5'-AGG TGC ACA CCA ATG TGG TG-3' (SEQ ID NO:8) and 5'-AAA AGC ACC GTG CAT GC-3' (SEQ ID NO:9). Second round PCR was cycled as follows: 92° C. for 3 min; 25 cycles of 92° C. for 40 s, 58° C. for 40 s, 72° C. for 40 s. All PCR reactions were performed in a "Genius" TECHNE system. Products (10 µL) of the PCR reactions were loaded on the 2% agarose gel and transferred (Vacuum Blotter, BioRad) to Zeta-Probe GT Blotting Membranes (BioRad). After UV crosslinking (Stratalinker, Stratagene) membranes were subjected to Southern hybridization procedure as suggested by the membrane manufacturer. The Southern probe was amplified from a plasmid with a cloned ASV genome using LTR primers 5'-CAA ATG GCG TTT ATT GTA TCG-3' (SEQ ID NO:10) and 5'-GAT TGG TGG AAG TAA GGT GG-3' (SEQ ID NO:11) and labeled with [α-$^{32}$P]dATP (ICN). Radioactive bands were detected overnight by exposure with Kodak BioMax MR film.

Apoptosis Assay with ATRkd-Expressing Cells.

GM847/ATRkd cells were treated with 5 µg/ml doxycycline, and the next day aliquots were either mock-infected or infected with the ASV IN+ or IN vectors [multiplicity of infection (moi) 10] in the presence of 5 µg/ml DEAE dextran. A fourth aliquot of these cells was treated with 50 µM ETP. Doxycycline was maintained in the medium after infection and ETP treatment. As a control, aliquots of GM847/ATRkd cells to which no doxycycline was added were treated in the same way. After 24 h, cells were harvested and stained with a terminal deoxynucleotidyltransferase-mediated dUTP nick end labeling (TUNEL) assay (In Situ Death Detection kit, Fluorescein, Roche Diagnostics). Stained cells were then quantitated by flow cytometry.

Chromatin Immunoprecipitation

Chromatin immunoprecipitation (ChIP) was performed as described (Boyd, K. E. & Farnham, P. J., Mol. Cell. Biol. 19:8393-8399, 1999; Orlando, V. TIBS 25:99-104, 2000). Briefly, at defined time points, infected and uninfected cells were treated with 1% formaldehyde to crosslink DNA and proteins. For Brca1 and Wrn analyses, nuclei were prepared and Brca1 and Wrn were immunoprecipitated from nuclear extracts with corresponding antibodies. DNA was then eluted from immunoprecipitates and amounts of total viral DNA (vDNA) in the nuclear extracts and vDNA immunoprecipitated with Brca1 and Wrn were determined by subjecting samples to standardized PCR with viral LTR probes, followed by agarose gel electrophoresis and Southern blotting with radioactively-labeled DNA probes. Filters were exposed to X ray film and results analyzed by a phosphorimager. The human Wrn antibody was a kind gift from Dr. Hiro Furiuichi and the Brca1 antibody was purchased from Santa Cruz Biotechnology, Inc.

For ChIP analyses, PCR can be performed with the following primers: 5'-AGC TCC AGG GCC CGG AGC GAC-3' (SEQ ID NO:12) and 5'-CTT CAA TGC CCC CAA AAC CAA-3' (SEQ ID NO:13).

Example 2

Figure 2A:
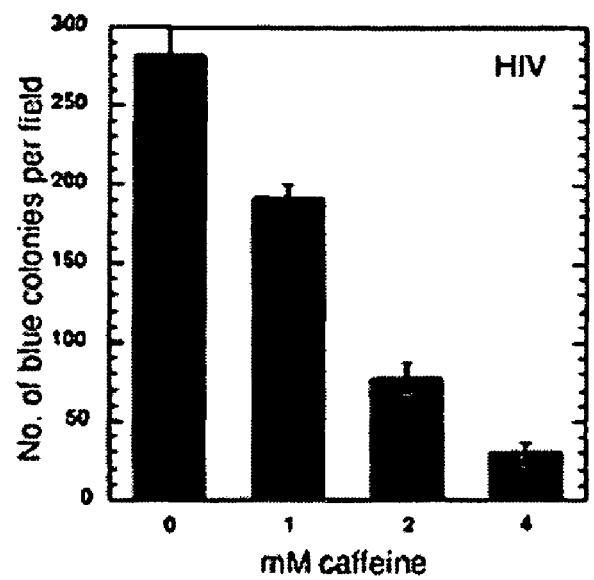
FIG. 2. Effect of caffeine on transduction by HIV-1- and ASV-based vectors. (A) HeLa cells were infected with the HIV-1-lacZ vector and exposed to caffeine for 24 hr. Five days post infection, cells were stained using a β-galactosidase assay and blue colonies were counted. (B) HeLa cells were infected with the ASV neo vector and exposed caffeine for 24 hr. After removal of caffeine, G418 was added to a final concentration of 1 mg/ml. G418-resistant colonies were counted 6 days post infection.

Stable Transduction of HeLa Cells by HIV-1-Based and ASV-Based Vectors is Inhibited by Caffeine To determine if caffeine can inhibit stable transduction by HIV-1, HeLa cells were infected with an HIV-1-based vector that expresses a lacZ reporter gene (Naldini et al., 1996, supra), in the presence of a range of concentration of the drug. Caffeine was added at the time of infection, and removed after 24 hr. Transduction was measured five to six days later by the presence of β-galactosidase positive colonies. The results showed a reduction in the number of cells stably transduced by the vector, with an $IC_{50}$ for caffeine estimated at 1.5 mM (FIG. 2A).

Figure 2B:
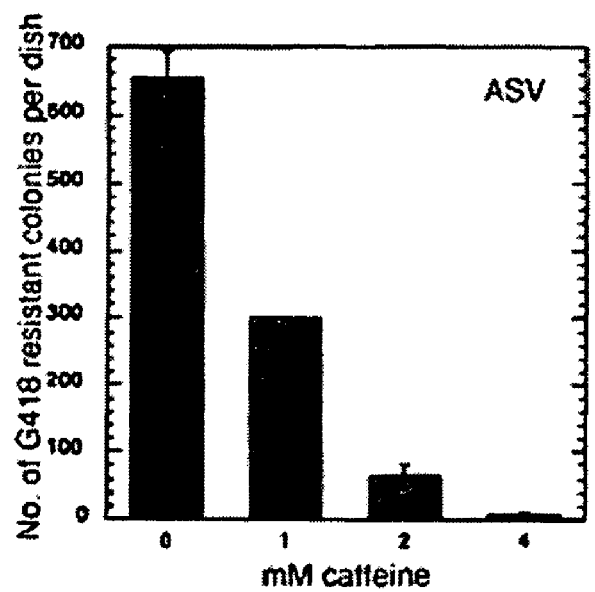

To determine if caffeine would inhibit stable transduction by another retrovirus, the protocol was repeated with an ASV-based vector (Daniel et al., 1999, supra) that carries a $neo^r$ reporter, and selected stable transductants after treatment with G418. As with HIV-1, a reduction in the number of cells stably transduced by the ASV vector was observed, with $IC_{50}$ approximately 0.8 mM (FIG. 2B).

Example 3

Figure 3A:
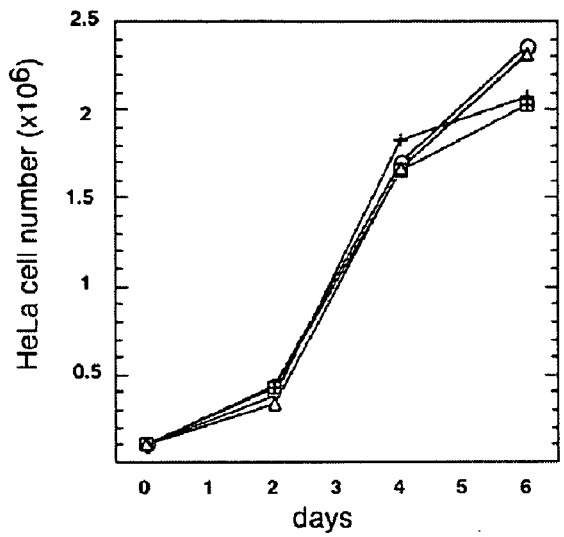
FIG. 3. Effect of caffeine on the growth and colony formation of uninfected HeLa cells and on expression of the $neo^r$ reporter. (A) Effect on cell growth. Cells were plated at a density of $10^5$ cells per 60 mm dish in the presence of increasing concentrations caffeine. The drug was applied to the cells for 24 hr and then removed. At indicated intervals, cells were harvested and viable cells counted. Open circles, no caffeine added; crosses, 1 mM caffeine; squares, 2 mM caffeine; triangles, 4 mM caffeine. (B) Effect on colony formation. 103 HeLa cells were plated on 60 mm dishes in the presence of caffeine; drug-containing medium was removed after 24 hr and colonies (triangles) were counted 9 days later. A population of ASV transduced, G418-resistant HeLa cells was plated at 103 per 60 mm dishes, in the presence of both caffeine and G418. Caffeine was removed after 24 hr, and G418 was retained in the medium continuously. Colonies (circles) were counted 8 days later. (C) Expression of the $neo^r$ reporter. A population of HeLa cells that had been stably transduced with the ASV vector carrying the $neo^r$ reporter gene was exposed to increasing concentrations of caffeine for 24 hr. The cells were then lysed and neomycin phosphotransferase II was detected by Western blot analysis. Lane 1, non-transduced HeLa cells, lanes 2-5, stably transduced HeLa cells.
Figure 3B:
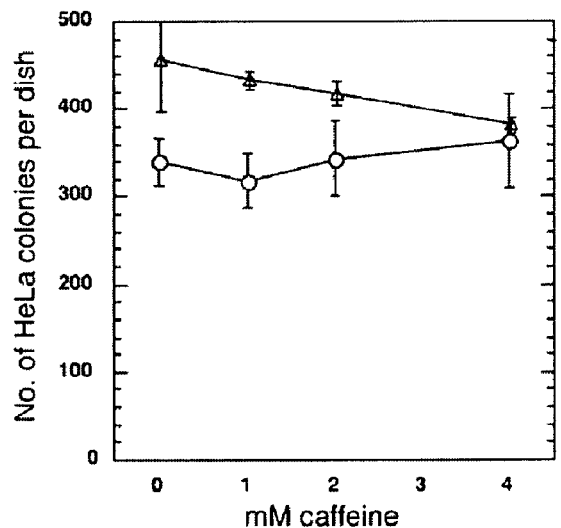

Lack of Effect of Caffeine on Inhibition of HeLa Cell Growth, Colony Formation and Expression of the Transduced Reporter Gene Under Conditions in Which Retroviral Transduction is Inhibited Caffeine has been reported to have no detectable effect on cell growth at 0.5-10 mM concentration (Zhu et al., J. Virol. 73: 3309-3316, 1999). Similar results were observed at 2 mM or 4 mM concentration (FIG. 3A). To test the effect of caffeine on colony formation, uninfected HeLa cells were plated at a low density and exposed them to the drug for 24 hr. The results showed that such treatment with caffeine had no significant effect on either colony number or colony size (not shown) at up to 4 mM concentration (FIG. 3B, triangles). Finally, the combined effects of G418 and caffeine treatment on colony formation by HeLa cells were examined. An ASV-$neo^r$-transduced, G418-resistant population of HeLa cells was treated with the concentration of G418 used to select resistant colonies, together with the indicated concentrations of caffeine. No effect on colony formation by HeLa cells under these conditions were observed (FIG. 3B, circles). Thus, inhibition of stable transduction by the ASV vector cannot be attributed to an effect on colony formation by the HeLa cells.

Figure 3C:
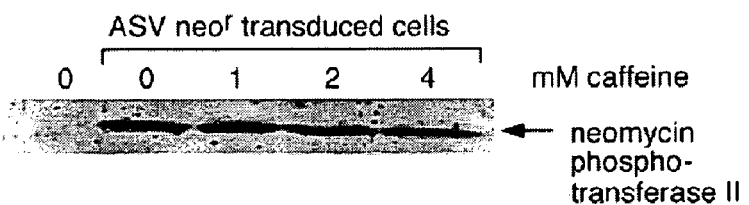

The effect of caffeine on stable transduction by expression of a retrovirus-transduced reporter in infected cells (FIG. 2), suggested the possibility that the observed reduction might be due to suppression of such expression following retroviral DNA integration. Therefore, the inventors investigated the effect of caffeine on production of the neomycin phosphotransferase protein in HeLa cells that had been stably transduced by the ASV vector. The results showed no reduction in the amounts of reporter protein after treatment of these cells for 24 hr with up to 4 mM caffeine (FIG. 3C).

Example 4

Effect of Caffeine on Viral DNA Synthesis, Nuclear Import, and Integration

To determine if caffeine affects the synthesis of viral DNA by reverse transcriptase, or other steps preceding reverse transcription, HeLa cells were infected with the ASV vector in the presence of caffeine and extracted extrachromosomal DNA at 24 hr post-infection. Synthesis of viral DNA was detected by quantitative PCR. Addition of caffeine at up to 4 mM final concentration had only a modest effect on the amount of viral DNA detected (FIG. 4A), which could not account for the observed reduction in transduction efficiency. Consistent with this result, similar concentrations of caffeine had no detectable effect on the activity of reverse transcriptase in permeabilized ASV particles.

Figure 4A:
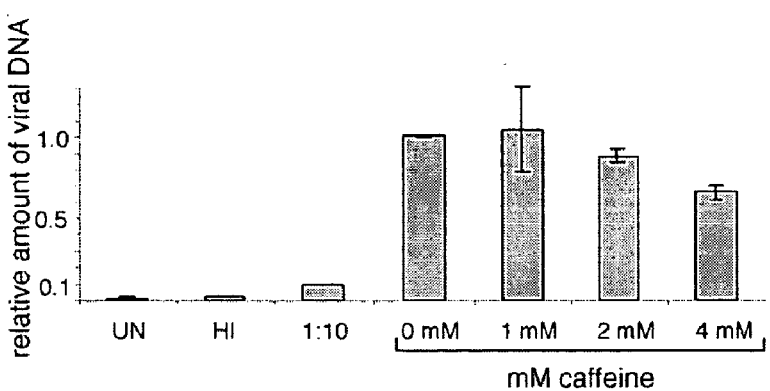
FIG. 4. Effect of caffeine on the synthesis of viral DNA, its nuclear import, and the yield of host-viral junction DNA. HeLa cells were infected with the ASV vector and treated with caffeine for 24 hr at which time cells were harvested. (A) Quantitation of viral DNA. Real time PCR was used to determine the amount of viral DNA relative to mitochondrial DNA. Cells were infected at m.o.i. 0.1 and the average of two independent experiments analyzed in duplicate are shown. UN, uninfected cells; HI, cells infected with the heat-inactivated virus; 1:10, cells infected with 1:10 dilution of the virus. (B) Nuclear import of viral DNA determined by formation of LTR-LTR circle junctions. The expected band is indicated by an arrow. Band intensity at 1 μl DNA was analyzed by a phosphorimager and is plotted in (D) as % intensity of circle junctions in the absence of caffeine. (C) Retroviral DNA integration. Detection of host-viral junction DNA. Covalent joining of viral and cell DNA in cells infected at m.o.i. 0.01 was evaluated by Alu-PCR. NP, no Alu primer in the first round of PCR (infection in the absence of caffeine); +, positive control (HeLa cells stably transduced by the ASV vector). Results were analyzed using a phosphorimager and are plotted in D as % intensity in the absence of caffeine. (D) Comparison of the affects of caffeine on the relative amounts of total, nuclear, and host-viral junction DNA in cells infected with the ASV vector based on quantitation of data in A, B, and C. Open circles and top curve, total viral DNA; open triangles and middle curve, nuclear viral DNA (circle junctions); filled circles and bottom curve, host-viral DNA junctions. The integrated DNA percentages represent an average of two experiments, one of which is shown in (C).
Figure 4B:
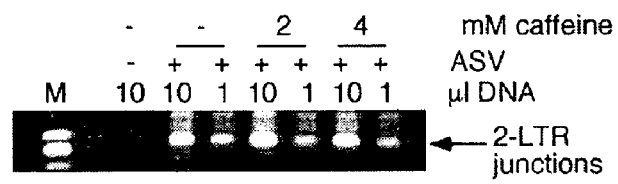

Caffeine may also affect the nuclear import of pre-integration complexes, a step that immediately precedes retroviral DNA integration. To test this possibility, the inventors determined the effect of the drug on formation of viral DNA circle junctions, which serve as a marker for nuclear import of pre-integration complexes. As shown in FIG. 4B, formation of circle junctions by the ASV vector was not significantly affected by 2 mM caffeine, and only a modest decrease, similar to that seen with total viral DNA, was observed at 4 mM caffeine.

Figure 4C:
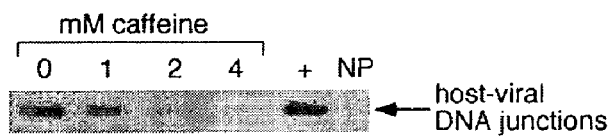
Figure 4D:
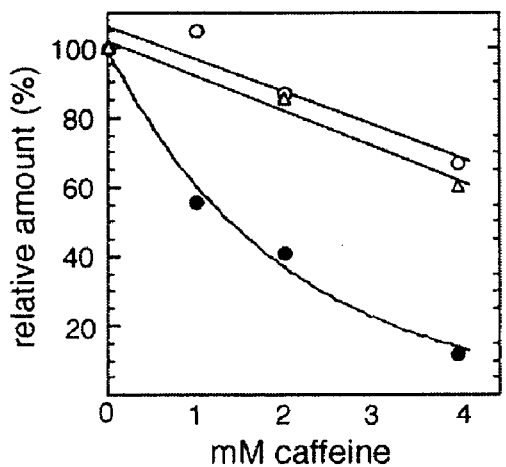

To determine whether caffeine affects the formation or stability of viral-host DNA junctions in vivo, HeLa cells were infected with the ASV vector, treated with caffeine, and integration was monitored 24 hr later using an Alu-PCR-based method (see Example 1). This method detects the covalent joining of viral and host DNA, irrespective of whether such junctions are repaired or unrepaired. The results showed a dose-dependent reduction in integration, with almost ten-fold (88%) inhibition in 4 mM caffeine (FIG. 4C, D), consistent with the observed reduction in the number of transductants shown in FIG. 2. Comparison of the relative amounts of total, nuclear, and integrated viral DNA, based on quantitation of the data in FIGS. 4A-C, is shown in FIG. 4D. The results are consistent with a selective inhibition of integration in the presence of caffeine and indicate either that the integrase-catalyzed processing or joining reactions (FIG. 1) are affected by caffeine, or that the integration intermediate is unstable in the presence of this DNA damage-sensitizing drug. Based on observations with non-homologous end-joining deficient cells (Daniel, R., Katz, R. A. & Skalka, A. M. (1999) Science 284, 644-647; Daniel, R., Katz, R. A., Merkel, G., Hittle, J. C., Yen, T. J. & Skalka, A. M. (2001) Mol. Cell. Biol. 21, 1164-1172), it may also be the case that unrepaired integration intermediates induce cell death, with a concomitant loss of these cells from the population.

Example 5

Figure 5:
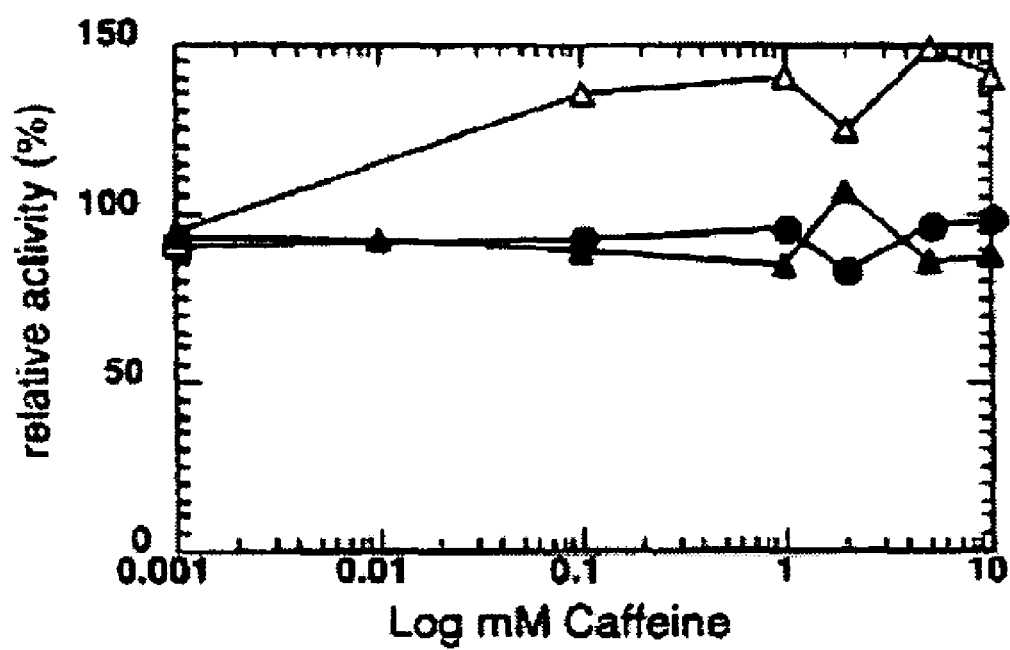
FIG. 5. Effect of caffeine on retroviral integrases in vitro. Processing and joining activities of ASV and HIV-1 integrases were assayed in vitro. Open triangles, ASV integrase joining activity; full circles, ASV processing activity; filled triangles, HIV-1 integrase processing activity.

Lack of Effect of Caffeine on the Activities of ASV and HIV-1 Integrases In Vitro It has been reported that retroviral integrase can be inhibited by treatment with caffeine-related compounds, such as dicaffeoylquinic acids (Pommier & Neamati, Antiviral Res. 52: 427-458, 1999; de Klein et al., Curr. Biol. 10: 479-482, 2000). These compounds also inhibit HIV-1 infection in cell culture (Pommier & Neamati, 1999, supra). To determine if caffeine inhibition of stable retroviral transduction is a consequence of its effect on retroviral integrases, the activities of HIV-1 and ASV integrases in vitro were assayed in the presence of this drug. As shown in FIG. 5, the processing and joining activities of ASV integrase and processing activity of HIV-1 integrase were unaffected by caffeine at up to 10 mM concentration. From these results it seems unlikely that the inhibitory effect of caffeine on stable integration and transduction can be explained by a direct effect on retroviral integrase.

Example 6

Stable Transduction of ATM-Deficient and ATM-Proficient Cells is Inhibited by Caffeine The major cellular targets of caffeine related to the DNA damage response are the ATM and ATR kinases (Zhou et al., 2000, supra; Blasina et al., 1999, supra; Hall-Jackson et al., 1999, supra; Sarkaria et al., 1999, supra). Because retroviral DNA transduction is normal in ATM-deficient cells (Daniel et al., 2001, supra), the data suggested that the caffeine effects observed were unlikely to reflect a requirement for ATM. To test this, the effect of caffeine on HIV-1 transduction of ATM-deficient and ATM-proficient cells was examined (Table 1). An ataxia telangiectasia (A-T) cell line was used in which ATM function was restored by stable transfection with an ATM-expressing plasmid; A-T cells stably transfected with an empty vector served as a control.

TABLE 1

Effect of caffeine on transduction of A-T cells that express an empty vector or a vector encoding ATM

| Cell line | | No. of lacZ-transduced (blue) colonies at caffeine concentration (mM) of: | | | |
|---|---|---|---|---|---|
| | | 0 | 1 | 2 | 4 |
| AT22IJE-T | (ATM−) | 284 | 171 (60)* | 88 (31) | 40(14) |
| AT22IJE-T/ATM | (ATM+) | 347 | 262 (76) | 144 (41) | 64(18) |
| AT22IJE-T/empty | (ATM−) | 313 | 234 (75) | 132 (42) | 46(14) |

*Numbers in parenthesis are percentages of colonies observed in absence of caffeine. Cells were infected with the HIV-1 (lacZ) vector and Lac+ (blue) colonies detected as described in Experimental Methods, supra; colony counts from two plates were averaged for each datum point.

As the inventors had observed previously, deficiency of ATM had no detectable effect on the efficiency of transduction by HIV-1 in the absence of caffeine. Furthermore, retroviral transduction was inhibited similarly by caffeine, regardless of the presence or absence of ATM.

Caffeine also inhibits a related kinase, mTOR, in vitro, at concentrations similar to those which inhibit ATM and ATR (Sarkaria et al., 1999, supra). To determine if mTOR is involved in retroviral transduction, the inventors infected HeLa cells and treated them with the mTOR-specific inhibitor, rapamycin. As no effect of this inhibitor on retroviral transduction was observed, it appears that mTOR is not required for efficient retroviral transduction. These data are consistent with the notion that it is the inhibition of ATR, and not ATM or mTOR, that leads to a reduction in the number or stability of integrated viral genomes after treatment with caffeine.

Example 7

Figure 6A:
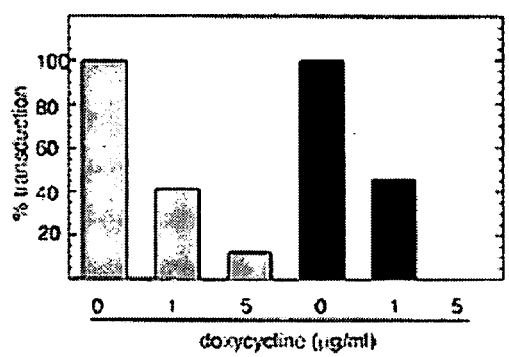
FIG. 6. Inhibition of ATR function leads to a reduction in the number of retroviral transductants and the yield of host-viral junction DNA. (A) Effect of expression of a dominant-negative ATR gene (ATRkd) on transduction by the HIV-1 vector. GM847/ATRkd cells were treated with doxycycline and infected. Two days after infection, cells were stained using the β-galactosidase assay and blue cells counted. Grey columns, cells infected with 10-2 dilution of the virus (m.o.i.
Figure 6B:
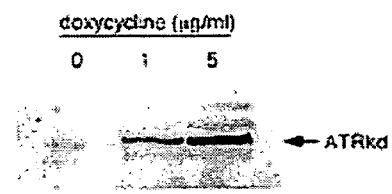
Figure 6C:
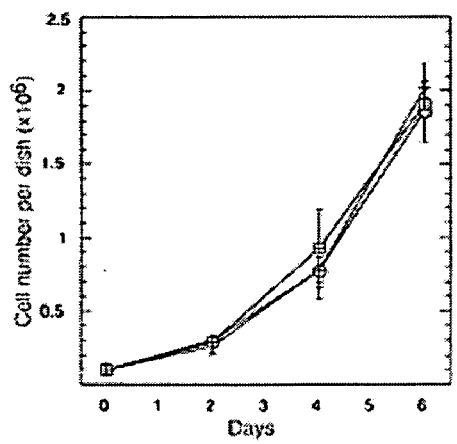
Figure 6D:
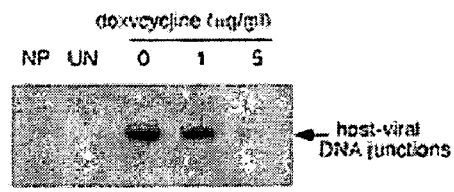

Reduction in Number of Stable Transductants Resulting from Overexpression of a Dominant-Negative ATR Mutant in Cells To examine the role of ATR more directly, the inventors examined the efficiency of retroviral DNA integration and transduction in cells defective in ATR function. Knockout of ATR is embryonic lethal in mice, and cells lacking ATR die in culture. Cells that synthesize the dominant-negative ATRkd protein (doxycycline-inducible expression) are viable, but show deficiencies in DNA repair that are distinct from those in cells deficient in ATM. As illustrated in FIG. 6A, cells expressing the ATRkd showed a dramatic, doxycycline-dependent reduction in the percentage of stable HIV-1 transductants with two concentrations of virus that differed ten-fold; similar results were observed with the ASV vector. These effects cannot be attributed to doxycycline alone, as treatment of parental cells with this drug had no effect on stable transduction (not shown). Furthermore, the reduction in transduction efficiency was correlated with the amount of the dominant-negative ATRkd protein present (FIG. 6B). As shown in FIG. 6C, expression of ATRkd had no significant effect on the cell growth rate. Thus, reduction in transduction efficiency by this vector could not be due to a general inhibition of cell growth. Finally, it was observed that, as with caffeine treatment, the relative amount of host-junction DNA, measured by Alu-PCR, was reduced upon overexpression of ATRkd (FIG. 6D), even though the amount of viral DNA was similar to that in the uninduced control (not shown). Thus, the caffeine target, ATR kinase, appears to be required for stable integration and efficient transduction by retroviral vectors. It may be the case that the integration process cannot be completed in the absence of normal ATR function and that all or some cells that contain unrepaired integration intermediates fail to survive the infection and are lost from the population.

Example 8

Infection of Cells that Express Dominant-Negative ATRkd Leads to Apoptosis

The inventors examined the viability of cells that overexpress ATRkd after viral infection. GM857/ATRkd cells were treated for 24 h with doxycycline to induce ATRkd synthesis, and samples were then mock-infected or infected with the ASV vector (IN+) or an integrase-defective derivative (IN−). The IN− virus is competent for all early steps of viral replication, but defective for the integrase-mediated steps in the integration process (FIG. 1). A fourth sample was treated with etoposide (ETP), a DNA topoisomerase II poison thought to generate DNA double-strand breaks throughout the cell cycle and shown to reduce the viability of ATRkd overexpressing cells (Cliby, W. A., Lewis, K. A., Lilly, K. K. & Kaufmann, S. H. (2002) J. Biol. Chem. 277, 1599-1606). Samples of uninduced cells were treated similarly as a control. The cultures were harvested 24 h later and the percentage of apoptotic cells was determined by terminal deoxynucleotidyltransferase-mediated dUTP nick end labeling and flow cytometry. The results (Table 2 and FIG. 7) show significant increases in the percentage of apoptotic cells after infection with the IN+ ASV and ETP treatment, when the cells were induced to overexpress ATRkd. In contrast, less or no increase in the apoptotic fraction was detected in the induced cells that were mock-infected or infected with the IN virus. These results support the notion that formation of the retroviral integration intermediate triggers a cellular DNA damage response. They also suggest that the yields of host-viral junction DNA and stable transductants are reduced in ATRkd overexpressing cells because, lacking normal ATR function, a significant fraction of such cells do not survive the damage induced by formation of the integration intermediate.

suggest that Brca1, or some component of a Brca1-dependent complex, may be required for formation or survival of stable transductants.

Example 11

Transduction of Nocodazole-Arrested 293T Cells is Sensitive to Caffeine

To determine if caffeine has any effect on HIV-1 transduction of non-dividing cells, exponentially dividing and nocodazole-arrested 293T cells were infected with an HIV-1-based vector. To arrest cells in M phase, cells were treated with nocodazole (1 µg/ml) for 24 hrs prior to addition of the virus. Nocodazole was maintained in the cell culture medium during and after infection. Cells were distributed in a 24-well plate at a density of $5 \times 10^4$ cells per well and nocodazole was

TABLE 2

Induction of apoptosis by retroviral infection of cells induced to overexpress ATRkd

|  | Mock-infected | ETP-treated | ASV(IN⁻)-infected | ASV(IN⁺)-infected |
| --- | --- | --- | --- | --- |
| Uninduced (−doxycycline) | 10.0 | 10.0 | 9.6 | 2.3 |
| Induced (+doxycycline) | 17.6 | 25.5 | 7.1 | 36.1 |
| Difference | 7.6 | 15.5 | <0 | 33.8 |

Doxycycline was added or not to GM847/ATRkd cells, and the following day the cells were infected at moi 10 with eitherASV vector (IN⁺) or with the integrase-deficient (IN⁻) vector, or treated with 50 µM etoposide, in the continued presence or absence of doxycycline. Twenty-four hours later, cells were stained using the TUNEL assay and analyzed as described in Experimental Methods. The percentage of cells that fell within the apoptotic window (see FIG. 7) is indicated.

Example 9

Association of ASV IN and ATR with Viral DNA

HeLa cells were infected and chromatin prepared at the indicated times (FIG. 8 A) or at 6 hours (FIG. 8 B) post-infection (pi). In (FIG. 8B) chromatin from cells infected with IN+ the IN− (D64E) mutant was analyzed. 0=no virus. Chromatin immunoprecipitation was performed as described in Boyd, K. E. & Farnham, P. J., Mol. Cell. Biol. 19:8393-8399, 1999; Orlando, V. TIBS 25:99-104, 2000, using antibodies (Ab) against ASV IN or ATR and viral DNA was detected using nested PCR with primers targeting viral LTR sequences.

Example 10

Evidence that Brca1 is Recruited to Sites of Retroviral DNA Integration

FIG. 9 shows results of a chromatin precipitation (CHIP) analysis using antibodies specific for human Wm and Brca1 proteins. The graph shows the percentage of viral DNA that is associated with each ChIP, corrected for the immunoprecipitation efficiency of each antibody. The association of Wm helicase with viral DNA peaks at 6 hours post-infection. This finding indicates that Wm is recruited to integration sites very rapidly. The present data also show that the ATR substrate Brca1 also associates with viral DNA, but only after about 8-10 hours post-infection. This CHIP data suggests different temporal patterns of association of repair proteins with sites of integration. Preliminary results from genetic assays also added to a final concentration of 1 µg/ml. Cells were infected 24 hrs later with the HIV-1 based vectors in the presence of 5 µg/ml DEAE dextran. Caffeine was added to cells along with the vector and maintained on cells for 24 hrs. Two days post-infection, cells were stained using a β-galactosidase assay (Stratagene according to manufacturer's protocol) and blue cells counted. To control for a possible caffeine contamination, 293T cells were also treated with caffeine from different sources (Upstate, USB). The results obtained were consistent with those observed with caffeine from Sigma.

Figure 10A:
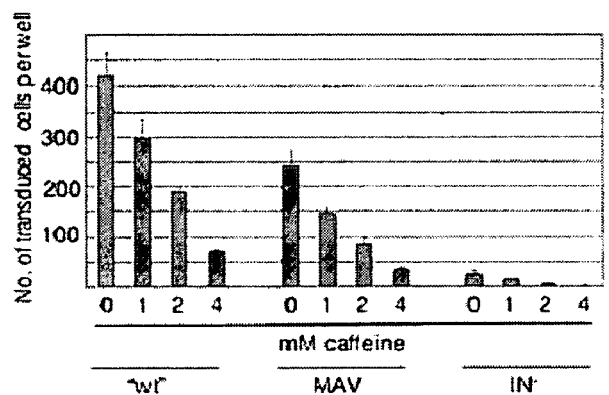
Figure 10B:
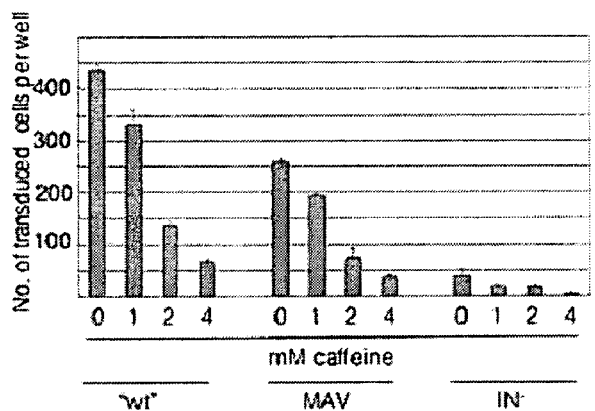

As shown in FIGS. 10A and 10B, caffeine inhibited HIV-transduction of the dividing (A) and nocodazole-arrested cells (B) in the same dose-dependent manner. Similar results were obtained with HeLa cells (data not shown). Caffeine also inhibited transduction by a multiply attenuated HIV-1-based vector which lacked the vpr, vif, vpu and nef genes FIGS. 10A and 10B. No caffeine cytotoxicity was observed under these conditions. To determine if the transduced lacZ gene was expressed from integrated vector DNA, 293T cells were infected with a vector carrying an inactivating D64V substitution in HIV-1 integrase. As shown in FIGS. 10A and 10B, this vector transduced 293T cells with about ten-fold lower efficiency than the vector carrying wild-type integrase.

Figure 10C:
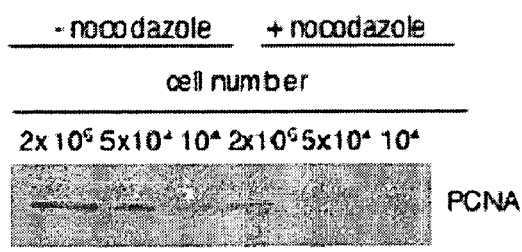

To determine the efficiency of the nocodazole arrest, cells were assayed for expression of the proliferating-cell nuclear antigen (PCNA) by Western blotting with an anti-PCNA antibody. PCNA accumulates in cells as they enter S phase, but is rapidly degraded in other phases of the cell cycle. (Takase, K et al. Reversible G1 arrest induced by dimethyl sulfoxide in human lymphoid cell lines: kinetics of the arrest and expression of the cell cycle marker proliferating cell nuclear antigen in Raji cells. Cell Growth Differ 1992, 3:515-521). FIG. 10C shows that the amount of PCNA in nocodazole-treated cells is only about 5% or less of that detected in exponentially dividing cells, indicating an efficient nocodazole-mediated growth arrest.

Figure 10D:
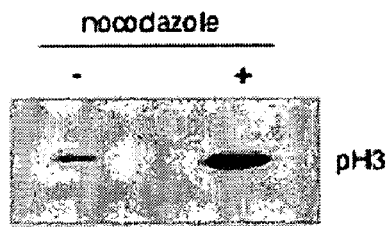

The phosphorylation of histone H3 on serine 10, which is tightly associated with mitosis, was also evaluated by Western blotting, using an anti-phosphorylated histone H3 (Ser 10) antibody (sc-8656-R; Santa Cruz). FIG. 10D reveals increased histone H3 phosphorylation on serine 10 of nocodazole-treated cells, consistent with the nocodazole-mediated mitotic arrest. To determine if the observed HIV-1 transduction occurred in the few cells that still divided, nocodazole-arrested 293T cells were infected with a high-titer vector, which resulted in transduction of approximately of the 25% cells in the absence of caffeine. However, caffeine reduced HIV-1 transduction efficiency even under these conditions (data not shown).

Example 12

Caffeine Reduces Transduction of Contact-Inhibited Mouse Embryo Fibroblasts

Because nocodazole inhibits cellular passage through the M phase, whether caffeine reduces transduction of cells arrested in G1 phase was investigated. Because agents that arrest cells in G1/S, such as aphidicolin and hydroxyurea, also trigger an ATR-dependent DNA damage response, mouse embryo fibroblasts (MEFs), which are very sensitive to contact inhibition, were used. MEFs were distributed in a 96-well plate at a density of $5 \times 10^4$ cells per well to prepare confluent cells, or at a density of $1 \times 10^4$ cells per well to obtain exponentially growing cells. The following day, the cultures were infected with the HIV-1-based vectors in the presence of 5 µg/ml DEAE dextran. Caffeine was added to cells at the same time as the vector and maintained in the medium for 24 hrs. Two days post-infection, cells were stained using a galactosidase assay (Stratagene protocol) and blue cells counted.

Figure 11A:
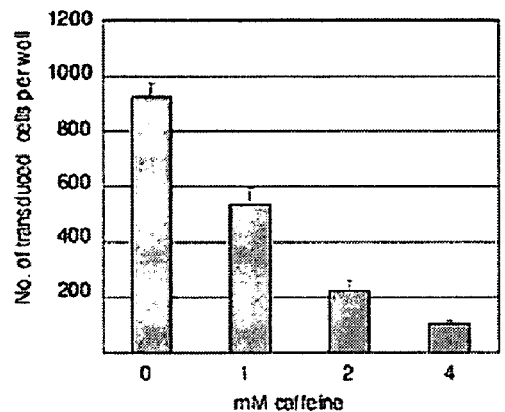
Figure 11B:
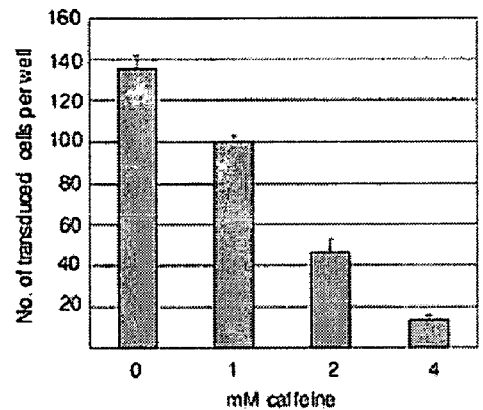
Figure 11C:
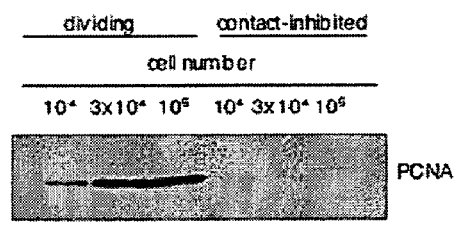
Figure 11D:
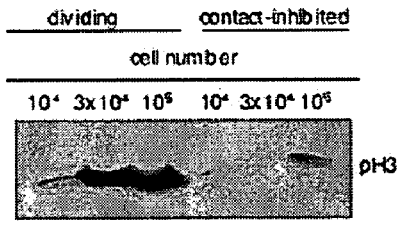

Contact inhibition of MEFs led to a substantial reduction in the absolute numbers of HIV-1-transduced cells (compare FIGS. 11A and 11B; cells were infected with the same amount of virus at the same time). However, transduction of both exponentially growing (A) and contact-inhibited (B) cells was further reduced by treatment with caffeine in a similar, dose-dependent manner. In each case, no caffeine-associated cytotoxicity was observed at the concentrations utilized. To confirm that contact inhibition of MEFs resulted in an efficient growth arrest, the level of the PCNA protein and phosphorylation (Ser 10) of histone H3 was evaluated by Western blotting. FIG. 11C shows that the amount of PCNA in contact-inhibited MEFs is only about 2% of that in exponentially dividing MEFs. A reduction in the amount of phosphorylated histone H3 was also observed (FIG. 11D), consistent with the MEF growth arrest.

Example 13

Caffeine Inhibits Transduction of Terminally Differentiated Neuronal Cells and Macrophages The effect of caffeine on transduction of naturally arrested human cells was investigated. Human peripheral blood mononuclear cells (PBMC) were isolated by centrifugation in Ficoll-Hypaque (Sigma, St. Louis, Mo., USA) from buffy coats of HIV-1 seronegative individuals. Monocyte-derived macrophages (MDM) were obtained from PBMC by adherence to plastic for 12 hours in DMEM supplemented with 10% human serum (Cellgro, Herndon, Va., USA), washed, and cultured in the same medium in the presence of macrophage colony-stimulating factor (MCSF, 2 ng/ml; Sigma, St. Louis, Mo., USA) for another 7-10 days, allowing cells to differentiate before infection. The medium was replaced twice during the incubation period. The primary cells were kept at 37° C. in a humidified incubator with 5% $CO_2$.

NT-2 neuronal precursor cells were purchased from Stratagene (Stratagene cloning system, La Jolla, Calif.), cultured, and differentiated into mature human neurons (over 95%) after treatment with retinoic acid, as described in Patel, C. A., et al. Lentiviral expression of HIV-1 Vpr induces apoptosis in human neurons. J Neurovirol 2002, 8:86-99; Patel, C. A., et al. Human immunodeficiency virus type 1 Vpr induces apoptosis in human neuronal cells. J Virol 2000, 74:9717-26; Pleasure, S. J., et al. NTera 2 cells: a human cell line which displays characteristics expected of a human committed neuronal progenitor cell. J Neurosci Res 1993, 35:585-602; and, Pleasure, S. J., et al. Pure, postmitotic, polarized human neurons derived from NTera 2 cells provide a system for expressing exogenous proteins in terminally differentiated neurons. J Neurosci 1992, 12:1802-15, each of which is herein incorporated by reference. Mature neurons generated by differentiating NT-2 cells were characterized by immunostaining for expression of ubiquitous neuronal markers (such as MAP2β and τ as well as phenotypically elaborating extensive neuritic processes identifiable as axons and dendrites.

To the human macrophages and neurons, caffeine was added along with the HIV-1-based vector in the presence of 5 µg/ml DEAE dextran. Caffeine was maintained on the cells for 24 hrs (macrophages) or 48 hrs (neurons) and β-galactosidase staining was performed two days post-infection.

Figure 12A:
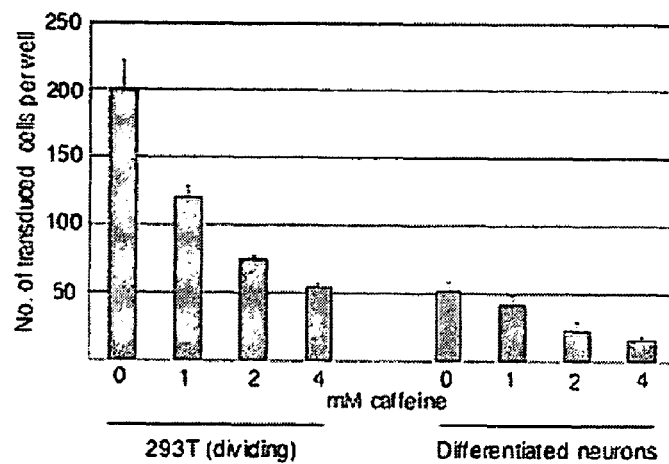
Figure 12B:
Figure 12C:
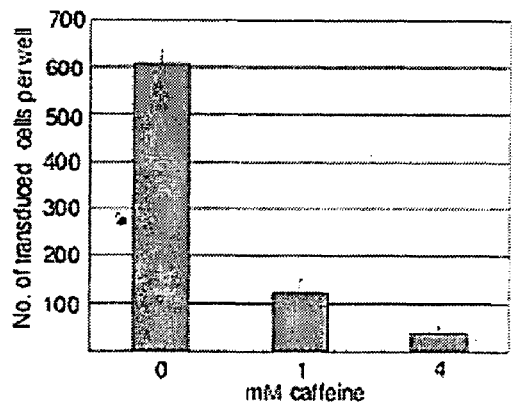

Terminally differentiated, post-mitotic neurons were infected with the HIV-1 vector. As shown in FIG. 12A, caffeine also reduced the efficiency of transduction of these cells with the HIV-1-based vector. To verify that the cells were not cycling, the amount of PCNA protein was measured. FIG. 12B shows that PCNA expression was not detected in these differentiated neuronal cells. Lastly, the effect of caffeine on transduction of terminally differentiated primary human macrophages was examined. As with the neurons, caffeine was found to inhibit transduction of these cells, under conditions that showed no visible cytotoxicity (FIG. 12C).

Example 14

Transduction of Nocodazole-Arrested Cells is Inhibited by Expression of the Dominant-Negative, Kinase-Dead ATR, ATRkd ATR is an essential gene; its knockout is embryonic lethal in mice and cultured cells die rapidly after the ATR gene is excised. (de Klein, A et al. Targeted disruption of the cell-cycle checkpoint gene ATR leads to early embryonic lethality in mice. Curr. Biol. 2000, 10:479-482). However, cells that express a dominant-negative, kinase-dead ATR protein (GM847/ATRkd) are viable, although they have deficiencies in DNA repair and/or checkpoint regulation (Cliby W. A. et al. Overexpression of a kinase-inactive ATR protein causes sensitivity to DNA-damaging agents and defects in cell cycle checkpoints. EMBO J. 1998, 17:159-169). In the cells used for these studies, the ATRkd gene is under control of a doxycycline-inducible promoter.

GM847/ATRkd cells were plated at a density of $2 \times 10^4$ cells per well of 24-well plate, in the presence or absence of doxycycline (5 µg/ml) and nocodazole (1 µg/ml). The following day, they were infected with the HIV-1-based vectors, again in the presence or absence of doxycycline and nocodazole, and, in the experiments described in Example 19 in the presence of caffeine. Doxycycline and caffeine were removed 24 hrs later, while nocodazole was maintained on the cells until two days post-infections, when the cultures were stained using the β-galactosidase assay.

Figure 13A:
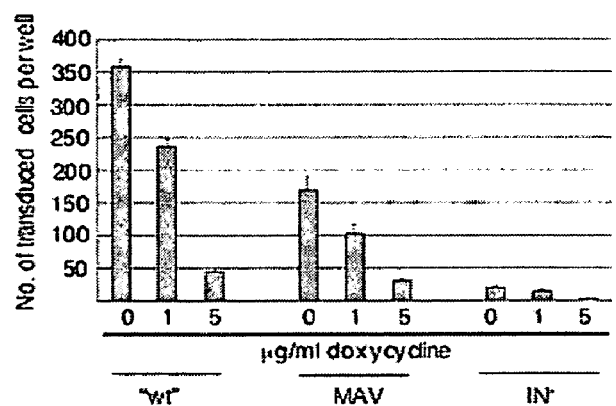

As shown in FIG. 13A, there is a doxycycline-dependent reduction in the percentage of dividing cells that are transduced by the HIV-1-based vector. Doxycline had no effect on transduction of parental GM847 cells (data not shown). Because ATR was also implicated in the regulation of Vpr-induced G2/M arrest, transduction of ATRkd-expressing cells by the multiply attenuated HIV-1-based vector was also evaluated. Reduced transduction of cells expressing the dominant negative ATRkd protein was observed, similar to that observed with the Vpr-containing HIV-1 vector (FIG. 10A).

Figure 13B:
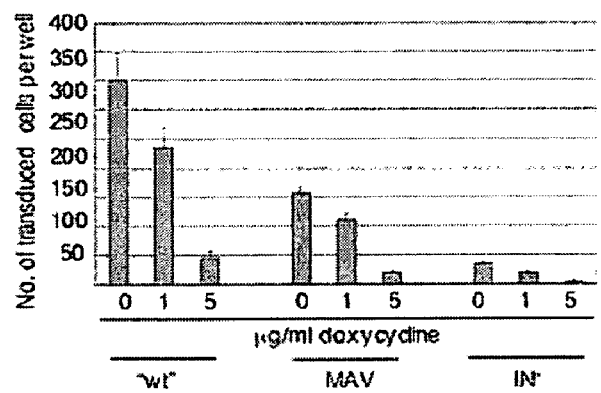
Figure 13C:
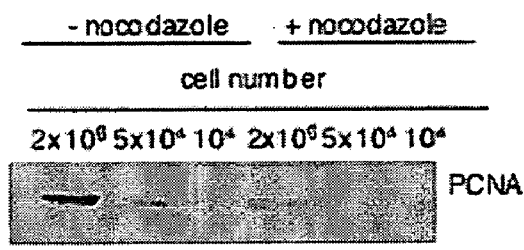
Figure 13D:
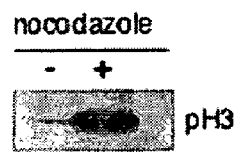

To examine the role of ATR in growth-arrested cells, the GM847/ATRkd cells were treated with nocodazole in addition to doxycycline. As shown in FIG. 13B, nocodazole-treated, ATRkd-expressing cells are transduced with HIV-1-based vectors at a reduced level, when compared to control nocodazole-arrested cells. As was the case with 293T cells, FIG. 13C shows that the amount of PCNA in nocodazole-treated cells is only about 10-20% of that in exponentially dividing cells, indicating an efficient nocodazole-mediated growth arrest. FIG. 13D shows an increase in histone H3 phosphorylation on serine 10 in nocodazole-treated cells, consistent with the nocodazole-mediated mitotic arrest.

Example 15

Residual HIV-1 Transduction of ATRkd-Expressing Cells is Relatively Resistant to Caffeine ATM and ATR kinases are reported to be two major cellular targets of caffeine and the HIV-1 transduction of ATM-deficient cells is inhibited by caffeine with the same efficiency as transduction of ATM-proficient cells. To determine if the residual transduction of ATRkd-expressing cells can be inhibited by caffeine, GM847/ATRkd cells were treated with doxycycline, infected with the HIV-1-based vector, and treated with caffeine. As shown in FIG. 14, caffeine inhibited HIV-1 transduction of GM847/ATRkd cells in the absence of doxycycline as efficiently as it inhibited transduction of 293T cells (FIG. 10). In the presence of doxycycline, the effect of caffeine was markedly different. Addition of 0.5 mM caffeine led to a 40% drop in transduction efficiency, regardless of the presence or absence of doxycycline. However, further increase in caffeine concentrations had little effect on transduction efficiency of doxycycline-treated, ATRkd-expressing cells. At the highest caffeine concentration, 4 mM, the transduction efficiency of doxycycline-treated cells was reduced only twofold when compared to control cells infected in the absence of caffeine. In contrast, addition of 4 mM caffeine led to a 9-fold reduction in transduction efficiency of GM847/ATRkd cells infected in the absence of doxycycline.

Example 16

Suppression of Replication of Different HIV-1 Strains by Methylxanthines

Human peripheral blood mononuclear cells (PBMCs) were isolated from HIV-1-seronegative individuals, and depleted of monocytes and CD8+ lymphocytes. CD8+ T-lymphocyte/monocyte-depleted PBMCs were cultured and infected with the T-cell-line-tropic HIV-1 NL4-3 (X4) strain, and simultaneously treated with the methylxanthines caffeine, theobromine, theophylline and paraxanthine obtained from Sigma Chemical Co. (St. Louis, Mo.). HIV-1 p24 antigen levels were assessed by ELISA at 3, 7 and 12 days post-infection, and positive cultures were defined as those demonstrating at least 30 μg/ml of HIV-1 p24 antigen in the cell culture supernatant. All procedures were performed under level P3 biosafety conditions to minimize the possibility of cross-contamination.

A 9-fold decrease in HIV-1 p24 antigen values was observed in samples treated with caffeine and theophylline (1,3-dimethylxanthine), when compared to control samples infected with NL4-3 alone (FIG. 15A). A three- to four-fold drop in HIV-1 p24 antigen levels was still observed at 7 days post-infection in samples treated with caffeine and theophylline, respectively. P24 antigen levels in caffeine- and theophylline-treated samples reached the control level at 12 days post-infection. A suppression of HIV-1 replication with paraxanthine (1,7-dimethylxanthine) and theobromine (3,7-dimethylxanthine) was also observed, however, these compounds suppressed HIV-1 replication only 2 to 3-fold at day 3 post-infection when compared with the untreated, NL4-3-infected control (FIG. 15A). Caffeine, theophylline and paraxanthine did not show any significant cellular cytotoxicity when evaluated by the XTT assay; only theobromine inhibited the PBMC growth by 40% at the utilized concentration (data not shown).

To determine if the effects of methylxanthines extend to different HIV-1 strains, a similar experiment with the macrophage-tropic (R5) HIV-1 strain, ADA, and the NL4-3 strain as a control was performed in parallel (FIG. 15B). Samples treated with lower methylxanthine concentrations, including 100 microM, which is a concentration close to that reached in the plasma of theophylline-treated patients [28-110 μM, (Ohnishi et al., 2003, Drugs Aging 20:71-84)], were also tested. Methylxanthines were added to the medium at the time of infection and maintained in the media until 6 days post-infection, when HIV-1 p24 antigen levels were analyzed. As shown in FIG. 15OA, methylxanthines inhibited replication of the rapidly-growing NL4-3 strain at 1 and 4 mM, but not at 100 microM (FIG. 15B, left panel). Caffeine and theophylline inhibited NL4-3 growth approximately 9-fold and 5-fold, respectively, at a concentration of 4 mM, whereas the effect of theobromine was much weaker (about a 2-fold inhibition), consistent with the data presented in FIG. 15A. Replication of the HIV-1 ADA strain was inhibited even at lower concentrations, with an $IC_{50}$ close to 60 microM (theophylline) and 100 microM (caffeine and theobromine) (FIG. 15B, right panel). The most efficient inhibitor of the HIV-1 ADA strain appeared to be theophylline, followed by caffeine and theobromine (FIG. 15B, right panel).

Example 17

Effect of Methylxanthines on Early Steps of the HIV-1 Life-Cycle

Figure 16A:
Figure 16A:
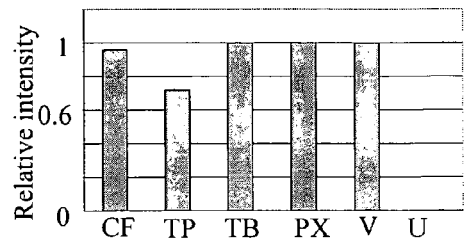

To determine which steps of the HIV-1 life-cycle are targeted by methylxanthines, the levels of HIV-1 DNA, HIV-1 nuclear import and HIV-1 DNA integration in infected, caffeine-treated cells were analyzed. To determine whether caffeine inhibits HIV-1 DNA synthesis or preceding stages of the HIV-1 life cycle, the levels of HIV-1 DNA were first determined (Nunnari et al., 2002, Aids 16:39-45; Otero et al., 2003, AIDS Res Hum Retroviruses 19:9237-41). PBMCs were infected with the HIV-1 strain NL4-3 and caffeine was added at the time of infection. Twenty-four hours after addition of the virus, cells were harvested and early steps of the HIV-1-life cycle analyzed by Southern blotting. As shown in FIG. 16A, methylxanthines, even at the highest utilized concentration (4 mM), did not have any significant negative effect on the level of HIV-1 DNA in infected and caffeine-treated cells.

Figure 16B:
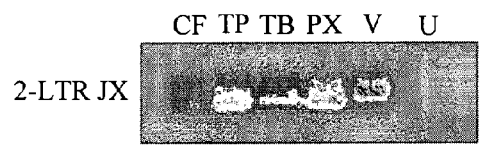
Figure 16B:
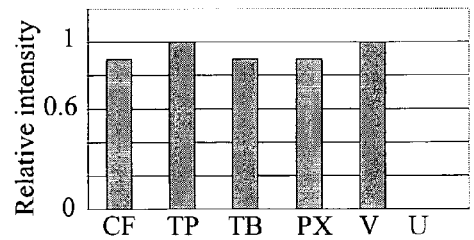
Figure 16C:
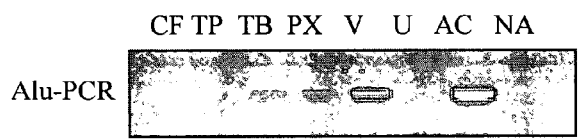
Figure 16C:
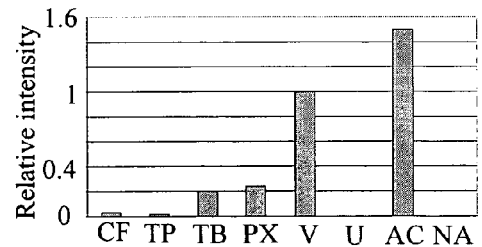

To determine if methylxanthines altered the nuclear import of HIV-1 pre-integration complexes (PICs), we analyzed the level of 2-LTR DNA junctions in infected cells by a quantitative DNA-PCR technique. The following sense and antisense primers were utilized: 5'-GTAACTAGAGA TACCCT-CAAC-3' (SEQ ID NO: 14) and 5'-CAGATCTGGTCTAACCAGAGA-3' (SEQ ID NO: 15). A specific primer that is contained in the amplicon of the 2-LTR DNA circle junction, 5'-AGTGGCGAGCCCTC AGATGCTGC-3' (SEQ ID NO: 16) was labeled with $^{32}P$ for Southern blotting analysis. To normalize the cell number, the human beta-globin gene was used as a standard (Nunnari et al., 2002, supra; Otero et al., 2003, supra). No significant inhibitory effect of caffeine on the level of 2-LTR junctions was demonstrated (FIG. 16B, data not shown). Then, the level of integrated HIV-1 DNA in these samples was determined by Alu-PCR in a PE 9700 system with 45 amplification cycles under conditions described in Example 1. As a positive control, ACH-2 cells, which carry one copy of latent, integrated proviral DNA in the cellular genome, were used. Comparison of caffeine-treated and control NL4-3 samples, revealed approximately 4- to 50-fold less integrated viral DNA in methylxanthine-treated samples (FIG. 16C).

Figure 16D:
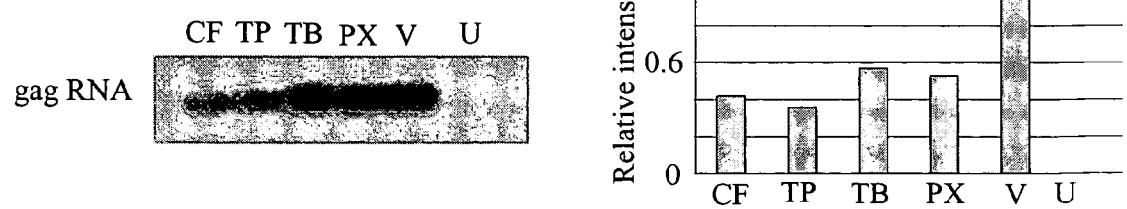
Figure 16E:
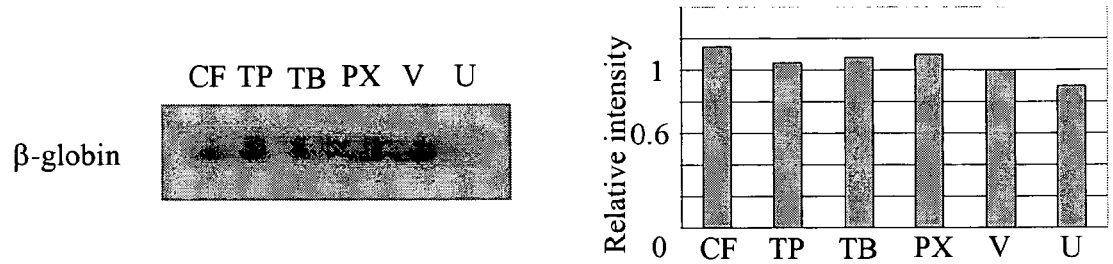

The level of unspliced HV-1-specific RNA in these cells was also investigated. Without being bound to any particular theory, it is believed that since integration begins to occur approximately 4-8 hrs post-infection, most HIV-1-specific RNA at the 24 hour time-point is likely due to expression of the integrated provirus. Intracellular unspliced viral RNA was analyzed utilizing a super-sensitive reverse transcriptase-polymerase chain reaction (RT-PCR) and Southern blotting assays for HIV-1 gag sequences. Southern blotting was utilized to visualize the specific bands and compared with a serially-diluted standard curve to quantitate viral unspliced RNA to 5 copies, with detection but not quantification between 1 to 5 copies, as described previously (Nunnari et al., 2002, supra). A decreased unspliced HIV-1-specific RNA level in cells treated with methylxanthines was observed, which correlates with the decreased levels of integrated HIV-1 DNA in these samples (FIG. 16D).

Example 18

Effect of Methylxanthines on Late Steps of the HIV-1 Life-Cycle

Figure 17A:
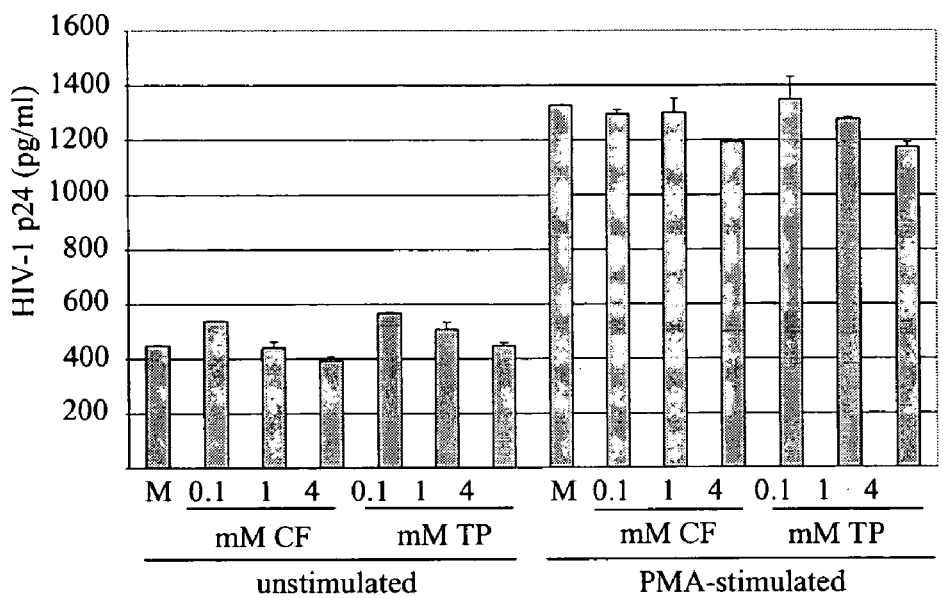
Figure 17B:
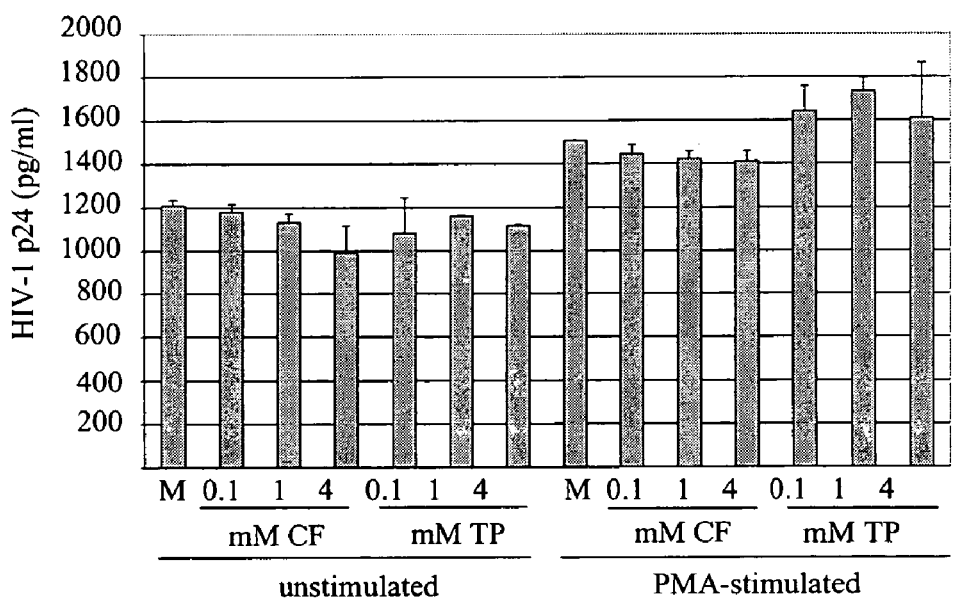

To determine if methylxanthines affect the late, post-integrative steps of the HIV-1 life-cycle, the ACH-2 line, which produces HIV-1 particles upon stimulation with phorbol myristate acetate (PMA), was used. Methylxanthines did not affect either production of HIV-1 virion particles in the culture supernatant, nor p24 antigen expression in unstimulated ACH-2 cells (FIGS. 17A and 17B). Likewise, methylxanthines had no effect on production of HIV-1 particles and intracellular p24 antigen levels when ACH-2 cells were stimulated with PMA (FIGS. 17A and 17B).

Example 19

Effect of Caffeine and Theophylline on Phosphorylation of ATM and ATR Substrates The cellular targets of caffeine are the ATM and ATR kinases. To establish if HIV-1 infection triggers the DNA damage response that is controlled by these kinases, human PBMCs were infected with the HIV-1 NL4-3 strain and analyzed by Western blotting to determine the levels of phosphorylation by ATM and ATR in these cells. Western blotting was sequentially performed with an anti pBRCA1 (Bethyl Laboratories, Montgomery, Tex., cat # A300-008A) or an anti-Ku86 antibody (Santa Cruz, sc-9034, Santa Cruz, Calif.). For detection of the p53 phosphorylated on serine 15 residue, Western blotting was performed with a rabbit polyclonal antibody from Cell Signaling Technology, Beverly, Mass. (cat # 9284S). As a positive control, dsDNA breaks were induced with the drug etoposide (ETP). Increased levels of p53 phosphorylated on serine 15 residue in infected cells, which is a well-established target of the ATM and ATR kinases (FIG. 18A) were observed. Similarly, increased phosphorylation of the BRCA1 protein on serine 1423 residue, which is also an ATR and ATM substrate, were observed (FIG. 18). p53 and BRCA1 phosphorylation were suppressed by addition of caffeine and also with theophylline (FIG. 18). These drugs failed to suppress a basal phosphorylation of BRCA1 on serine 1423 (FIG. 18, left lanes), suggesting a role of caffeine-resistant kinase in this process.

The contents of each patent, patent application and publication cited or described in this document are hereby incorporated herein by reference, in their entirety.

The present invention is not limited to the embodiments described and exemplified above, but is capable of variation and modification without departure from the scope of the appended claims.

What is claimed:

1. A method of identifying agents that inhibit retroviral DNA integration into host DNA, wherein the agents inhibit the retroviral DNA integration by inhibiting production or activity of host cellular ATR kinase, the method comprising:
   a. combining a test compound suspected of inhibiting the production or activity of ATR kinase with ATR kinase and a downstream target of ATR kinase activity; and
   b. measuring an effect of the test compound on the product of ATR kinase reactivity with the downstream target, as compared with an equivalent sample not exposed to the test compound, wherein a decrease in production of the product is indicative that the test compound is an inhibitor of ATR kinase production or activity.

2. The method of claim 1, wherein the test compound is an antibody, antagonist, reverse agonist, antisense nucleic acid, DNA binding protein, methylxanthine or a metabolite or derivative of a methylxanthine.

3. A method of identifying agents that inhibit retroviral DNA integration into host DNA, wherein the agents inhibit the retroviral DNA integration by inhibiting production or activity of host cellular ATR kinase or a downstream target of ATR kinase, comprising:
   a. combining a test compound suspected of inhibiting production or activity of ATR kinase or a downstream target of ATR kinase with cultured transducible host cells and a retroviral vector encoding a detectable gene product, under conditions wherein stable transduction of the host cells with the retroviral vector results in production of the detectable gene product; and
   b. measuring the amount of detectable gene product produced, as compared with an equivalent sample not exposed to the test compound, wherein a decrease in production of the gene product in the presence of the test compound is indicative that the test compound inhibits retroviral integration by inhibiting production or activity of ATR kinase or a downstream target of ATR kinase.

4. The method of claim 3, wherein the retroviral vector is human immunodeficiency virus (HIV) or human T-cell leukemia virus (HTLV).

5. The method of claim 3, wherein the detectable gene product is beta-galactosidase, placental alkaline phosphatase, secreted embryonic alkaline phosphatase, luciferase, chloramphenicol acetyltransferase, beta-glucuronidase, green fluorescent protein, red fluorescent protein, yellow fluorescent protein, cyan fluorescent protein, cerianthus orange fluorescent protein, or a protein that confers drug resistance.

6. The method of claim 3, wherein the cultured transducible host cells are human cells.

7. The method of claim 3, wherein the test compound is an antibody, antagonist, reverse agonist, antisense nucleic acid, DNA binding protein, methylxanthine or a metabolite or derivative of a methylxanthine.

8. A method of identifying agents that inhibit retroviral DNA integration into host DNA wherein said retroviral DNA integration is independent of ATM, wherein the agents inhibit the retroviral DNA integration by inhibiting production or activity of host cellular ATR kinase, the method comprising:
   a. combining a test compound suspected of inhibiting the production or activity of ATR kinase with ATR kinase and a downstream target of ATR kinase activity; and
   b. measuring an effect of the test compound on the product of ATR kinase reactivity with the downstream target, as compared with an equivalent sample not exposed to the test compound, wherein a decrease in production of the product is indicative that the test compound is an inhibitor of ATR kinase production or activity.

* * * * *